(12) United States Patent
Terstappen et al.

(10) Patent No.: US 7,056,657 B2
(45) Date of Patent: Jun. 6, 2006

(54) APPARATUS AND METHODS FOR MAGNETIC SEPARATION

(75) Inventors: Leon W.M.M. Terstappen, Huntingdon Valley, PA (US); Gerald V. Doyle, Wynnewood, PA (US); Paul A. Liberti, Huntingdon Valley, PA (US); Gerald J. Dolan, Hungtingdon Valley, PA (US)

(73) Assignee: ImmuniVest Corporation, Wilmington, DE (US)

( * ) Notice: Subject to any disclaimer, the term of this patent is extended or adjusted under 35 U.S.C. 154(b) by 571 days.

(21) Appl. No.: 10/068,712

(22) Filed: Feb. 6, 2002

(65) Prior Publication Data

US 2002/0141913 A1 Oct. 3, 2002

Related U.S. Application Data

(62) Division of application No. 09/376,686, filed on Aug. 18, 1999, now Pat. No. 6,361,749.

(60) Provisional application No. 60/098,021, filed on Aug. 18, 1998.

(51) Int. Cl.
C12Q 1/70 (2006.01)

(52) U.S. Cl. .............................. 435/5; 435/2; 435/7.2; 435/7.21; 435/7.5; 435/7.9; 435/7.94; 435/971; 436/526; 436/531; 436/534; 436/807; 436/824; 436/827; 436/828; 209/214; 209/223.1; 210/222; 210/695

(58) Field of Classification Search .................... 435/5, 435/2, 7.2, 7.21, 7.5, 7.9, 7.94, 971; 436/526, 436/531, 534, 807, 824, 827, 828; 209/214, 209/223.1; 210/222, 695
See application file for complete search history.

(56) References Cited

U.S. PATENT DOCUMENTS

| | | | |
|---|---|---|---|
| 3,567,026 A | 3/1971 | Kolm | |
| 3,676,337 A | 7/1972 | Kolm | |
| 3,902,994 A | 9/1975 | Maxwell | |
| 3,970,518 A | 7/1976 | Giaever | |
| 4,017,385 A | 4/1977 | Morton | |

(Continued)

OTHER PUBLICATIONS

"The Properties of Magnetic Supports in Relation to Immobilized Enzyme Reactions", Robinson et al., Biotechnology & Bioengineering, vol. XV, pp. 603-606 (1973).

(Continued)

Primary Examiner—Long V. Le
Assistant Examiner—Pensee T. Do
(74) Attorney, Agent, or Firm—Joseph F. Aceto; James L. Wilcox

(57) ABSTRACT

Separation apparatus and method for separating magnetic and/or magnetically-labeled particles from a test medium.

Test medium within a reaction chamber is caused to flow past a collecting surface, and a high-gradient magnetic field is applied to the surface to capture magnetically responsive particles in the test medium. The particles are deflected toward the collection surface by baffles, a spinner, or a sprayer, or are funneled past the surface by a plunger operable to be displaced into close proximity to the surface to provide a narrow flow path for the particle-laden test medium. The particles normally suspended in the medium are separated out of suspension by adhesion to the collection surface. The particles may be resuspended by removal of the surface from the high-gradient field, or removal of the high-gradient field from the surface. The collection surface is a thin-walled non-magnetic material having a plurality of magnetic pole faces positioned therearound.

13 Claims, 18 Drawing Sheets

U.S. PATENT DOCUMENTS

| | | |
|---|---|---|
| 4,018,886 A | 4/1977 | Giaever |
| 4,042,492 A | 8/1977 | Decker |
| 4,230,685 A | 10/1980 | Senyei |
| 4,267,234 A | 5/1981 | Rembaum |
| 4,420,390 A | 12/1983 | Carr |
| 4,452,773 A | 6/1984 | Molday |
| 4,554,088 A | 11/1985 | Whitehead |
| 4,659,678 A | 4/1987 | Forrest |
| 4,663,029 A | 5/1987 | Kelland |
| 4,686,501 A | 8/1987 | Palmier |
| 4,795,698 A | 1/1989 | Owen |
| 5,053,344 A | 10/1991 | Zborowski |
| 5,101,980 A | 4/1992 | Arvidson |
| 5,108,933 A | 4/1992 | Liberti |
| 5,186,827 A | 2/1993 | Liberti |
| 5,200,084 A | 4/1993 | Liberti |
| 5,224,604 A | 7/1993 | Duczmal |
| 5,316,151 A | 5/1994 | Thompson |
| 5,466,574 A | 11/1995 | Liberti |
| 5,512,332 A | 4/1996 | Liberti |
| 5,541,072 A | 7/1996 | Wang |
| 5,597,531 A | 1/1997 | Liberti |
| 5,636,747 A | 6/1997 | Hettinger |
| 5,663,051 A | 9/1997 | Vlasselaer |
| 5,691,208 A | 11/1997 | Miltenyi |
| 5,698,271 A | 12/1997 | Liberti |
| 5,779,892 A | 7/1998 | Miltenyi |
| 5,795,470 A | 8/1998 | Wang |
| 5,823,354 A | 10/1998 | Elkind |
| 5,976,369 A | 11/1999 | Howe |
| 5,985,153 A | 11/1999 | Dolan |
| 5,993,665 A | 11/1999 | Terstappen |
| 6,103,113 A | 8/2000 | Saho |
| 6,190,619 B1 * | 2/2001 | Kilcoin et al. ............ 422/131 |

OTHER PUBLICATIONS

"Magnetic Solid-Phase Radioimmunoassay", Hersh et al., Clinica Chemica Acta, 63, pp. 69-72 (1975).

"High Gradient Magnetic Separation Theory and Applications", R.R. Oder, IEEE Transactions on Magnetics, vol. Mag;-12, No. 5, pp. 428-435 (1976).

"Magnetite-Protein Conjugates for the Separation of Cells by High Gradient Magnetic Filtration", Owen et al, Cell Separation: Methods and Selected Applications, vol. 4, pp. 259-275 (1987).

"Magnetic Separation Techniques; Their Application to Medicine", Kemshead et al, Molecular and Cellular Biochemistry, 67, pp. 11-18 (1985).

* cited by examiner

APPARATUS AND METHODS FOR MAGNETIC SEPARATION

RELATED APPLICATIONS

This application is a division of application Ser. No. 09/376,686, filed Aug. 18, 1999 now U.S. Pat. No. 6,361,749, which claims the priority of U.S. Provisional Application No. 60/098,021, filed Aug. 18, 1998.

FIELD OF THE INVENTION

The present inventions relates to the field of bioparticle isolation. More specifically, the invention provides novel magnetic separation devices and methods for isolating magnetically labeled substances of interest from a non-magnetic test medium by means of high gradient magnetic separation (HGMS).

BACKGROUND OF THE INVENTION

Magnetic separators and methods of separation of magnetic particles from non-magnetic media have been described for use in a variety of laboratory and clinical procedures involving biospecific affinity reactions. Such reactions are commonly employed in testing biological samples, such as bodily fluids like blood, bone marrow, leukapheresis products, spinal fluid or urine, for the determination of a wide range of target substances, especially biological entities such as cells, proteins, nucleic acid sequences, and the like.

As used herein, the term "target substance" refers to any member of a specific binding pair, i.e. a pair of substances or a substance and a structure exhibiting a mutual affinity of interaction and includes such things as cells, cell components, biospecific ligands and receptors. "Ligand" is used herein to refer to substances, such as antigens, haptens and various cell-associated structures, having at least one characteristic determinant or epitope, which is capable of being biospecifically recognized by and bound to a receptor. "Receptor" is used herein to refer to any substance or group of substances having biospecific binding affinity for a given ligand, to the substantial exclusion of other substances. Among the receptors determinable via biospecific affinity reactions are antibodies (both polyclonal and monoclonal), antibody fragments, enzymes, nucleic acids, C1q, peptides, lectins, protein A/G, single chain antibodies and the like. The determination of any member of a biospecific binding pair is dependent upon its selective interaction with the other member of the pair.

Various methods are available for determining the above-mentioned target substances based upon complex formation between the substance of interest and its specific binding partner. Means are provided in each instance whereby the occurrence or degree of target substance/binding partner complex formation is determinable.

Small magnetic particles have proved to be quite useful in analyses involving biospecific affinity reactions, as they are conveniently coated with biofunctional polymers, e.g., proteins, provide very high surface areas, and give reasonable reaction kinetics. Magnetic particles ranging from 0.7–1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunologic reagents, having reasonably good suspension characteristics when mildly agitated. Insofar as is known, however, without some degree of agitation, all of the magnetic particles presently in commercial use settle in time and must be resuspended prior to use. This adds another step to any process employing such reagents.

Small magnetic particles, such as those mentioned above, generally fall into two broad categories. The first category includes particles that are permanently magnetized; and the second comprises particles that become magnetic only when subjected to a magnetic field. The latter are referred to herein as magnetically responsive particles. Materials displaying strong magnetically responsive behavior are sometimes described as paramagnetic. However, certain ferromagnetic materials, e.g., magnetic iron oxide, may be characterized as magnetically responsive when the crystal size is about 300 Å or less in diameter. Larger crystals of ferromagnetic materials, by contrast, retain permanent magnet characteristics after exposure to a magnetic field and tend to aggregate thereafter. See P. Robinson et al., *Biotech Bioeng.* XV:603–06 (1973).

Magnetically responsive colloidal magnetite is known. See U.S. Pat. No. 4,795,698 to Owen et al., which relates to polymer-coated, sub-micron size magnetite particles that behave as true colloids.

The magnetic separation apparatus/method used for bound-free separations of target substance-bearing magnetic particles from test media will depend on the nature and particle size of the magnetic particle. Micron size ferromagnetic, i.e., permanently magnetized, particles are readily removed from solution by means of commercially available magnetic separation devices. These devices employ a single relatively inexpensive permanent magnet located externally to a container holding the test medium. Examples of such magnetic separators are the MAIA Magnetic Separator manufactured by Serono Diagnostics, Norwell, Mass., the DYNAL MPC-1 manufactured by DYNAL,Inc., Great Neck, N.Y. and the BioMag Separator, manufactured by Advanced Magnetics, Inc., Cambridge, Mass. A specific application of a device of this type in performing magnetic solid-phase radioimmunoassay is described in L. Hersh et al., *Clinica Chemica Acta*, 63: 69–72 (1975). A similar magnetic separator, manufactured by Ciba-Corning Medical Diagnostics, Wampole, Mass. is provided with rows of bar magnets arranged in parallel and located at the base of the separator. This device accommodates 60 test tubes, with the closed end of each tube fitting into a recess between two of the bar magnets.

Colloidal magnetic materials are not readily separable from solution as such, even with powerful electro-magnets but, instead, require high gradient field separation techniques. See, R. R. Oder, *IEEE Trans. Magnetics,* 12: 428–35 (1976); C. Owen and P. Liberti, *Cell Separation: Methods and Selected Applications*, Vol. 5, Pretlow and Pretlow eds., Academic Press, NY, (1986); J. T. Kemshead and J. Ugelstad, *Magnetic Molecular and Cellular Biochem.,* 67, 11–18 (1985). The gradient fields normally used to filter such materials generate huge magnetic forces. Another useful technique for performing magnetic separations of colloidal magnetic particles from a test medium, by various manipulations of such particles, e.g., addition of agglomerating agents, described in U.S. Pat. No. 5,108,933.

High gradient magnetic separation (HGMS) is typically accomplished by using a device having a separation chamber in which a wad of magnetic stainless steel wire is disposed between the poles of a conventional electro- or superconducting-magnet and serves to generate large field gradients around the wire which exert a strong attractive force on target substance-bearing magnetic particles. A commercially available high gradient magnetic separator of the type described immediately above is the MACS device made by Miltenyi Biotec GmbH, Gladbach, West Germany, which employs a column filled with a non-rigid steel wool matrix in cooperation with a permanent magnet. In operation, the enhanced magnetic field gradient produced in the vicinity of the steel wool matrix attracts and retains the magnetic particles while the non-magnetic test medium passes through and is removed from the column. Similar magnetic separators employing a steel wool matrix for separating colloidal size magnetic components from a slurry containing the same are also disclosed in U.S. Pat. Nos. 3,567,026, 3,676,337 and 3,902,994. In the last mentioned patent, the separator is provided with a magnetic wool matrix capable of movement into and out of the influence of a magnetic field as a continuously moving element.

It has been found that the steel wool matrix of such prior art HGMS devices often gives rise to nonspecific entrapment of biological entities, other than the target substance, which cannot be removed completely without extensive washing and resuspension of the particles bearing the target substance and multiple passages through the device. Moreover, the size of the column in many of the prior art HGMS devices requires substantial quantities of experimental materials, which limits their use in performing various important laboratory-scale separations. In addition, the steel wool matrix may be harmful to certain sensitive cell types.

A useful magnetic separator that avoids problems identified above is described in U.S. Pat. No. 5,200,084. The separator of this patent comprises magnetic means featuring a pair of confronting magnets external to the container and a magnetic gradient intensifying means positioned within a container holding the test medium. The magnetic particles adhere to the magnetic means within the container which serves to separate or remove the particles from the test medium.

U.S. Pat. No. 4,663,029 relates to an HGMS device which is stated to be an improvement with respect to devices employing a magnetic wool matrix as the magnetic field gradient intensifier, as well as to devices relying on differences in magnetic susceptibility of particles in a fluid to effect separation. The U.S. Pat. No. 4,663,029 patent describes an apparatus for continuous magnetic separation of particles from a slurry according to their magnetic moment, by passing the slurry through a separator comprising a non-magnetic canister with a magnetized wire or rod extending adjacent to the canister. The wire is magnetized by a magnetic field to create a magnetization component transverse to the longitudinal axis of the wire, thereby to provide a field gradient extending "everywhere" within the canister space and exerting a radial force on particles passing through the canister. Depending upon the orientation of the magnetic field relative to the canister, diamagnetic particles in the slurry can be attracted toward the wire and paramagnetic particles repelled, or vice versa, for a magnetic field usually rotated by 90° with respect to the plane of the canister.

The magnetic separator described in U.S. Pat. No. 5,466,574 and manufactured by Immunicon comprises at least one container and magnetic means capable of generating a high gradient magnetic field in the test medium within the container. The container has a peripheral wall with an internal surface area and is adapted to receive the test medium with the magnetically responsive colloidal particles therein.

If the test medium being separated is in a steady state, e.g., in a batch-type operation, suitable containers include microtiter wells, test tubes, capillary tubes closed at one end, or other nonmagnetic cylindrical walled vessels defining a chamber for performing the desired separation. Furthermore, a plurality of test samples may be processed simultaneously through the use of a carrier capable of holding more than one sample container. In a preferred form, the carrier includes means for holding a plurality of containers around the periphery of the carrier.

If the test medium is to pass continuously through the separator, a suitable container is a conduit or tube having openings at each end. Such containers are preferably non-magnetic, e.g., glass or plastic, and of cylindrical configuration.

In a particularly preferred embodiment, the magnetic field generating means may comprise sets of four or six permanent magnets or electro-magnets. The magnets are arranged so as to define a cavity which accommodates the container. In this embodiment, the polarity and positioning of the magnets located on the opposite sides of the cavity are such as to produce flux lines which generate a high gradient magnetic field within the test medium in the container. The magnets may be housed in a ferromagnetic yoke, usually of cylindrical configuration, which serves to enhance the field strength produced by the apparatus. The magnetic field gradient produced by this "multipole" arrangement is characterized by a very strong magnetic field near the edge of the cavity and by virtually no magnetic field at the center of the cavity.

The physical properties of the magnetic particles preferably used in the practice of U.S. Pat. No. 5,466,574, particularly the relatively small particle size, permit a level of operating efficiency which, insofar as is known, has not been achievable heretofore. Furthermore, by controlling the quantity of magnetic particles added to the test medium, relative to the exposed surface area of the wall of the container in contact with the test medium and controlling the orientation of such exposed surface, so as to be substantially coextensive with the flux lines of the magnetic field, it is possible to cause the magnetic particles to adhere along the exposed surface of the container wall in a substantially single layer, corresponding in thickness of about the size of the magnetic particles and any substance or material borne thereby. By operating in this way, occlusion of nonspecifically bound substances in the immobilized magnetic particles is virtually negligible.

In separating magnetically responsive colloidal particles from a non-magnetic test medium in accordance with the methods of the invention described in the U.S. Pat. No. 5,466,574 patent, the particles are initially dispersed in the non-magnetic test medium, forming a stable suspension therein. The magnetic particles typically comprise a receptor capable of specific binding to a target substance of interest in the test medium. If it is desired to separate target substances from test medium in a steady state, a suitable container holding the test medium and the receptor-magnetic particle conjugates are placed in the magnetic separator for batch-wise processing. The external magnetic means disposed around the container produce a magnetic field gradient in the test medium, which causes the magnetic particles to move toward the wall and to become adhered thereto.

In the method of U.S. Pat. No. 5,466,574 which employs a plurality of containers held in a carrier, the magnetic field gradient causes the magnetically responsive colloidal particles in the test medium to move toward and adhere to the wall of each container closest to the magnetic means. In accordance with this method, the orientation of the wall of each container in the carrier relative to the magnetic means may be adjustable to cause the particles to adhere more uniformly around the wall of each container.

In another embodiment of the method of the '574 invention, the test medium being separated may be flowed through the separator. The magnetic field gradient intensifying means produces an "open" field gradient of sufficient strength to pull the magnetic particles from the test medium moving at a pre-determined rate and to adhere them to the wall. The non-magnetic test medium is discharged from the container at the outlet end. In a related embodiment of this method, in which the container includes one or more baffles, the test medium to be separated is poured into the inlet opening at one end of the conduit. As the test medium moves through the flow path in the conduit, the magnetic particles in the test medium are attracted by the magnetic means toward the wall of the conduit and the flow thereby comes in contact with the baffles. The baffles are arranged to deflect the particles carried in the flow toward the wall of the separation vessel. The magnetic means may be operable to cause the particles to become adhered to the interior wall of the separation vessel, or to permit particles to move down the wall for collection at one or more outlets provided along the periphery of the wall at the end opposite the inlet. The test medium may be removed at an outlet laterally spaced from the particle outlet(s) in the center portion of the conduit at the end opposite the inlet end.

In carrying out the methods of U.S. Pat. No. 5,466,574, the non-magnetic test medium may be removed from the separator while the magnetic particles are retained on the walls of the container and subjected to further processing, as desired. By performing analyses involving biospecific affinity reactions in this way, resuspension of the magnetic particles bearing the target substance is effectively obviated. Accordingly, this method substantially reduces the processing time required for, and thus the cost of, bioanalytical testing.

Although the field gradients achieved in the devices described in the '574 patent significantly improve the ability to entrap magnetic, colloidal particles, they are still generally inadequate to collect colloidal magnetic particles with still smaller sizes (perhaps below about 100 nm). They do not have sufficient gradients to effectively collect magnetically labeled target substances in cases where the total number of the probes or magnetic colloids attached to the targets is low i.e. where the effective magnetic moments of the targets are low. In addition the separation of the magnetically labeled target substances in these devices is facilitated by the forming of chains of magnetic particles while in the magnetic field which effectively increase the magnetic moment of the targets.

From the foregoing review of the prior art, it is apparent that HGMS affords certain advantages in performing medical or biological analyses based on biospecific affinity reactions involving colloidal magnetic particles. Nevertheless, it would be desirable to provide HGMS apparatus and methods which are of relatively simple construction and operation, relying only on gradient intensifying means external to the separation chamber, and yet maximizing magnetic field gradients, and which reduce entrapment of non-target substances and eliminate loss of immobilized target substance due to shear forces or collisions with other biological entities. Such a development would clearly be of practical utility in conducting various laboratory-scale separations, particularly in cell separations.

SUMMARY OF THE INVENTION

It is an object of this invention to provide improved magnetic separation apparatus and methods capable of generating a high gradient magnetic field within a non-magnetic test medium to separate magnetically responsive colloidal particles from the test medium.

The present invention provides a novel apparatus for separating magnetically responsive particles from a non-magnetic test medium which provides a collection surface having a high magnetic field strength, and which maximizes the clumping or build-up of the particles on the collection surface.

More specifically, the present invention provides a chamber having a size to facilitate test reactions, and having means to deflect particles resulting from the reactions toward the collection surface.

In a preferred embodiment, the present invention provides a container with a collection surface, and a plunger displaceable into close proximity to the collection surface to direct particles in the test medium toward the collection surface.

The apparatus of the present invention comprises novel arrays of pole faces disposed to provide a high gradient magnetic field along the collection surface. Preferably the pole faces may be displaced outwardly away from the collection surface during resuspension so as to reduce the magnetic attraction of the particles to the collection surface without imparting magnetic forces upon the particles tending to displace them parallel to the collection surface.

These and other objective of the invention will become apparent in the following description.

DETAILED DESCRIPTION OF THE INVENTION

Figure 1A:
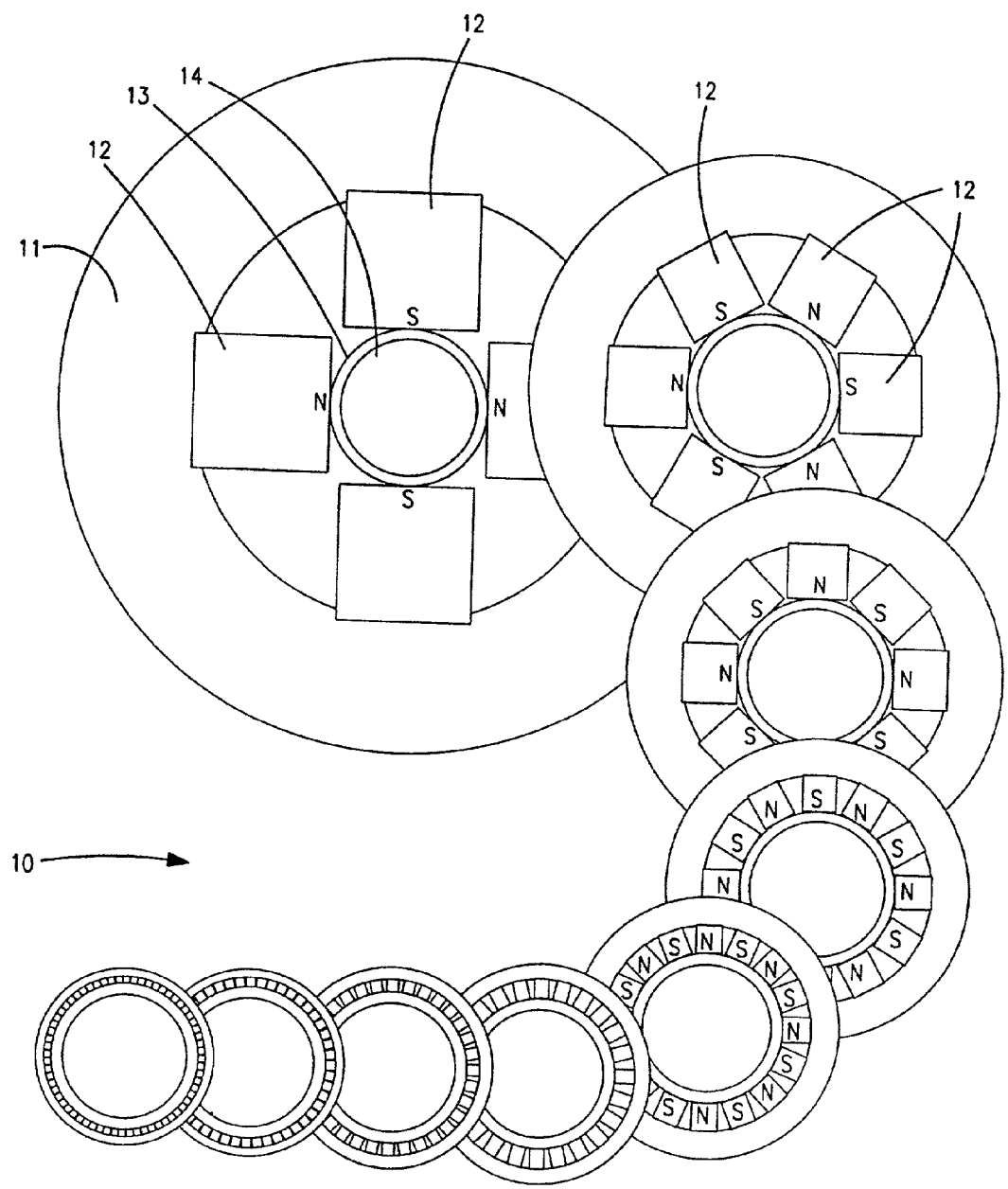
FIG. 1a is a diagrammatic view of nine magnetic separation systems embodying the present invention.

In the separation of target substances from a heterogeneous mixture using receptors that identify a ligand on the target substances, one can directly or indirectly label the receptors with magnetic colloids or particles. While large magnetic particles (1–10 um) have the advantage that they can be separated in magnetic devices with relatively low magnetic gradients such as manufactured by Dynal (Dynal-MPC-1) the disadvantage of such particles is that they do not have colloidal properties. This results in the need to continuously mix the sample and in the inability to effectively find the targets when present at low density (concentration), and particularly when at low concentration compared to coexistent particles in the same fluid. Moreover they obstruct the observation of the target substance because of their larger size and consequently one needs to dissociate the particle from its target. Colloidal magnetic particles with small sizes, perhaps below 200 nm, do not have these disadvantages but their magnetic moment is often insufficient to respond productively in most low gradient, open field magnetic devices. To increase the gradients which permit these colloidal magnetic particles and the targets substance on which they are bound to be separated, open field magnetic separators, which utilize 4 or 6 opposing magnets, have previously been described (U.S. Pat. No. 5,466,574).

An alternative approach is to use internal magnetic field gradient sources such as manufactured by Immunicon (Pin separator) and Miltenyi (Minimax). The principle of these devices is to induce local high gradients by placing materials such as steel wool, iron beads or pins between the magnets. In internal gradient magnetic devices, the gradients are high and close to the ferromagnetic material sources, but fall quickly with increasing distance from them as illustrated in Table 1 for saturated magnetic cylinders. The analogous gradients are stronger and the drop-off faster for spheres of the same diameters.

TABLE 1

A cylindrical wire inside a uniform magnetic field of 10 Kg (nominally chosen value) would provide gradients outside of it (but internal to the cylinder which contains it). The value of the gradient depends on the size (diameter) of the wire and the distance (R) from the wire center. This table presents values along a line which passes through the cylinder center and is parallel to the externally supplied field. The indicated values would be observed for wires with an arbitrarily chosen wire saturation magnetization of 12 kg (kg = kilogauss = 1000 gauss). Many present rare earth alloy magnets are close to this value; iron is closer to 20 kg. The values for this common metal would be proportionality higher.

| | Diameter of wires | | | | |
|---|---|---|---|---|---|
| Distance from wire center (R) | 0.2 µm grad B (Kg/cm) | 2.0 µm grad B (Kg/cm) | 20 µm grad B (Kg/cm) | 0.2 mm grad B (Kg/cm) | 2 mm grad B (Kg/cm) |
| 0.1 µm | 600,000 | — | — | — | — |
| 0.2 µm | 75,000 | — | — | — | — |
| 0.5 µm | 4,800 | — | — | — | — |
| 1.0 µm | 600 | 60,000 | — | — | — |
| 2.0 mm | 75 | 7,500 | — | — | — |
| 5.0 µm | 4.8 | 480 | — | — | — |
| 10.0 µm | 0.6 | 60 | 6,000 | — | — |
| 20.0 µm | 0.075 | 7.5 | 750 | — | — |
| 50.0 µm | 0.0048 | 0.48 | 48 | — | — |
| 0.10 mm | 0.0006 | 0.06 | 6.0 | 600 | — |
| 0.20 mm | 0.000075 | 0.0075 | 0.75 | 75 | — |
| 0.50 mm | 0.0000048 | 0.00048 | 0.048 | 4.8 | — |

TABLE 1-continued

A cylindrical wire inside a uniform magnetic field of 10 Kg (nominally chosen value) would provide gradients outside of it (but internal to the cylinder which contains it). The value of the gradient depends on the size (diameter) of the wire and the distance (R) from the wire center. This table presents values along a line which passes through the cylinder center and is parallel to the externally supplied field. The indicated values would be observed for wires with an arbitrarily chosen wire saturation magnetization of 12 kg (kg = kilogauss = 1000 gauss). Many present rare earth alloy magnets are close to this value; iron is closer to 20 kg. The values for this common metal would be proportionality higher.

| | Diameter of wires | | | | |
|---|---|---|---|---|---|
| Distance from wire center (R) | 0.2 μm grad B (Kg/cm) | 2.0 μm grad B (Kg/cm) | 20 μm grad B (Kg/cm) | 0.2 mm grad B (Kg/cm) | 2 mm grad B (Kg/cm) |
| 1.0 mm | . . . | 0.00006 | 0.006 | 0.6 | 60 |
| 2.0 mm | . . . | . . . | 0.00075 | 0.075 | 7.5 |
| 5.0 mm | . . . | . . . | 0.000048 | 0.0048 | 0.48 |

$B = [B_{ext}(m - 1) D^2]/[4(m + 1)R^2] = 2 \Pi MD^2/4R^2$ (I)
$\text{grad } B = [B_{ext}(m - 1)D^2]/[4(m + 1)R^3] = 2 \Pi MD^2/4R^3$ (II)
where D = the diameter of a circular wire
R = the distance from the center of the wire
M = the wire magnetization
m = the magnetic permeability of the wire
$B_{ext}$ = the magnitude of the externally applied field perpendicular to the wire
B = the magnitude of the wire resultant field contribution along a line passing through its center
grad B = the magnitude of the resultant field gradient outside the wire at a distance R from its center.

Table I lists the magnitude of the magnetic gradient as a function of the distance, R, from the center of cylindrical ferromagnetic wires of different diameters. The gradients are determined by Maxwell's equations, which produce equations I and II for the strength of the magnetic field outside the wires and the gradient of the field. The equations give the magnitudes of these quantities when the wire has an internal magnetization per unit volume of M. If the wires are composed of "soft" ferromagnetic materials, the magnetization depends on the value, $B_{ext}$, an externally applied field. For any value of M, for a "hard" or "soft" ferromagnetic material with constant, uniform magnetization, the dependence on the distance and wire diameter are as shown. The gradient values listed in Table 1 assume a typical wire magnetization such that 4ΠM=12 kiloGauss (Kg), a value close to that of a certain rare earth magnetic alloy.

Table 1 demonstrates that for a narrower wire, the field gradient at the surface of the wire is larger than for thicker wires, although the magnitude of the gradient falls off much more rapidly with distance from the wire in the construction of magnetic filters. The rapid fall-off is lessened by incorporating a number of ferromagnetic objects and by placing them close to each other, thus achieving a high gradient over most of the relevant volume. The disadvantage of these devices is the accompanying reduction in volume being treated and the potential of undesired entrapment of non-target substances between the structures. Further, magnetic target substances are often difficult to recover. In addition the separation vessels, including the ferromagnetic structures, may be used only once, and the desired re-suspension of the target substances from the vessels requires a volume at least as high as the volume of the vessel resulting in sample dilution which cannot be reduced below an amount defined by this chamber volume.

In contrast to internal gradient separation systems external separation systems provide a significant number of advantages such as: 1. Separations can be performed in simple vessels such as laboratory test tubes, centrifuge tubes or even blood vacutainers. 2. Reactions can be performed on collected target materials and by re-introducing the sample into the magnetic device a simple means for washing is afforded. 3. Such vessels are readily engineered into automated systems as existing "off the shelf" handling equipment is available. 4. Volume reduction can readily be accomplished merely by resuspending the collected material into a smaller volume. There is however significant drawback which is that open field gradient systems of gradient magnitudes similar to those in Table I have never been generated in a means where they can be used efficiently. Based on the foregoing, however, it is clear that open field separators are desirable providing that sufficient gradients can be obtained. It is further desirable to perform radial separations so as to 1) utilize as much separation surface (and avoid piling up) and 2) so as to minimize non-specific entrapment. Towards these ends a computer model has been generated for determining gradients within simple vessels as a function of the number of radially placed magnets as in the quadrupole or hexapole devices described. In the course of that modeling several important discoveries were made which are:

(1) In both the quadrupole and the hexipole arrangements the magnetic gradient is essentially constant over nearly the entire radius (excepting the region very near the center) of the device:

(2) As the number of radial magnets is increased the magnetic gradient is indeed related to the radius being highest near the magnet pole faces; and (3) When the gradients nearest the magnet surface are plotted as a function of magnet number the values go through a maximum.

Figure 1B:
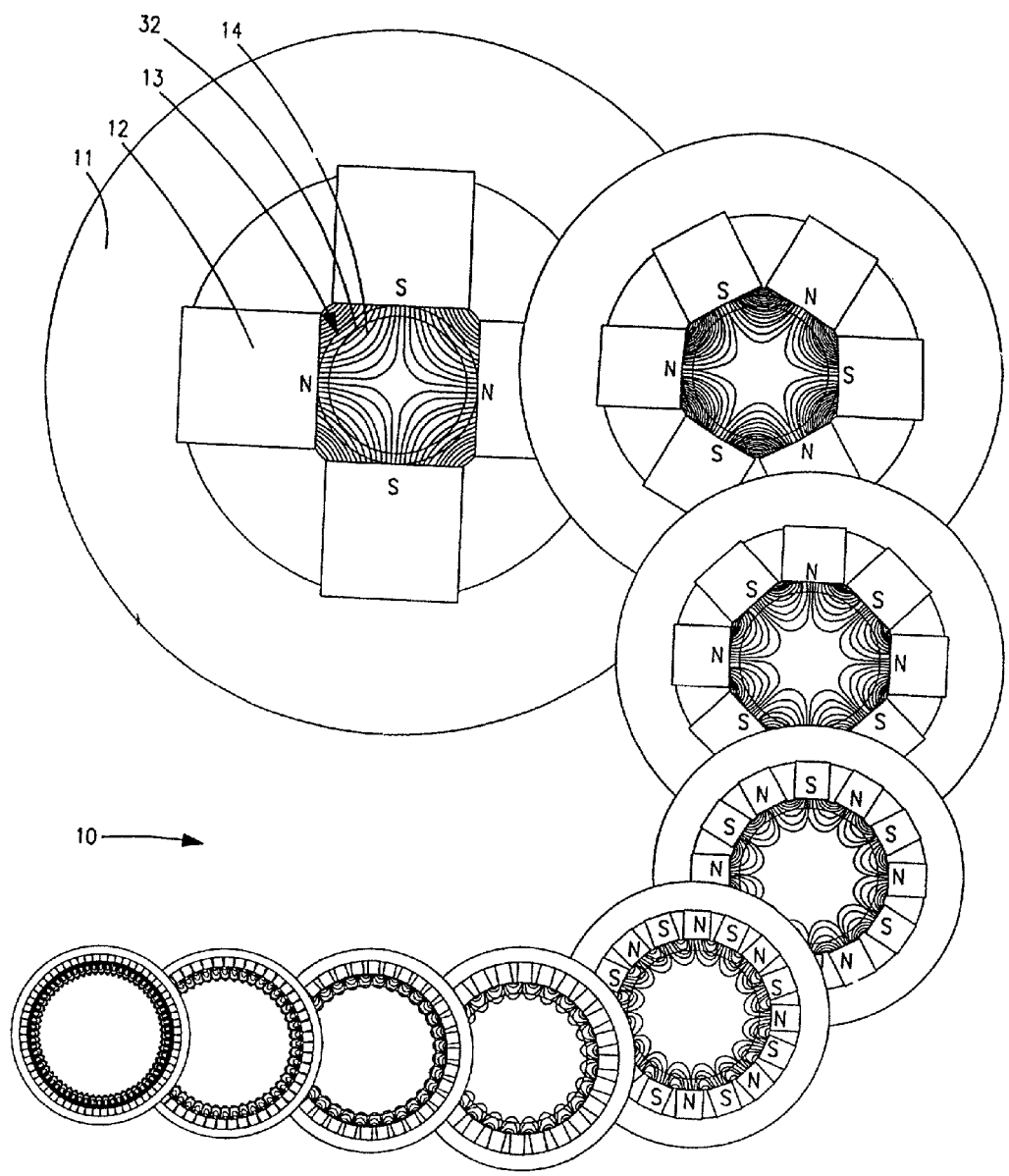
FIG. 1b is a view similar to FIG. 1a but with the magnetic field lines generated by the magnetic poles plotted in each vessel.
Figure 1C:
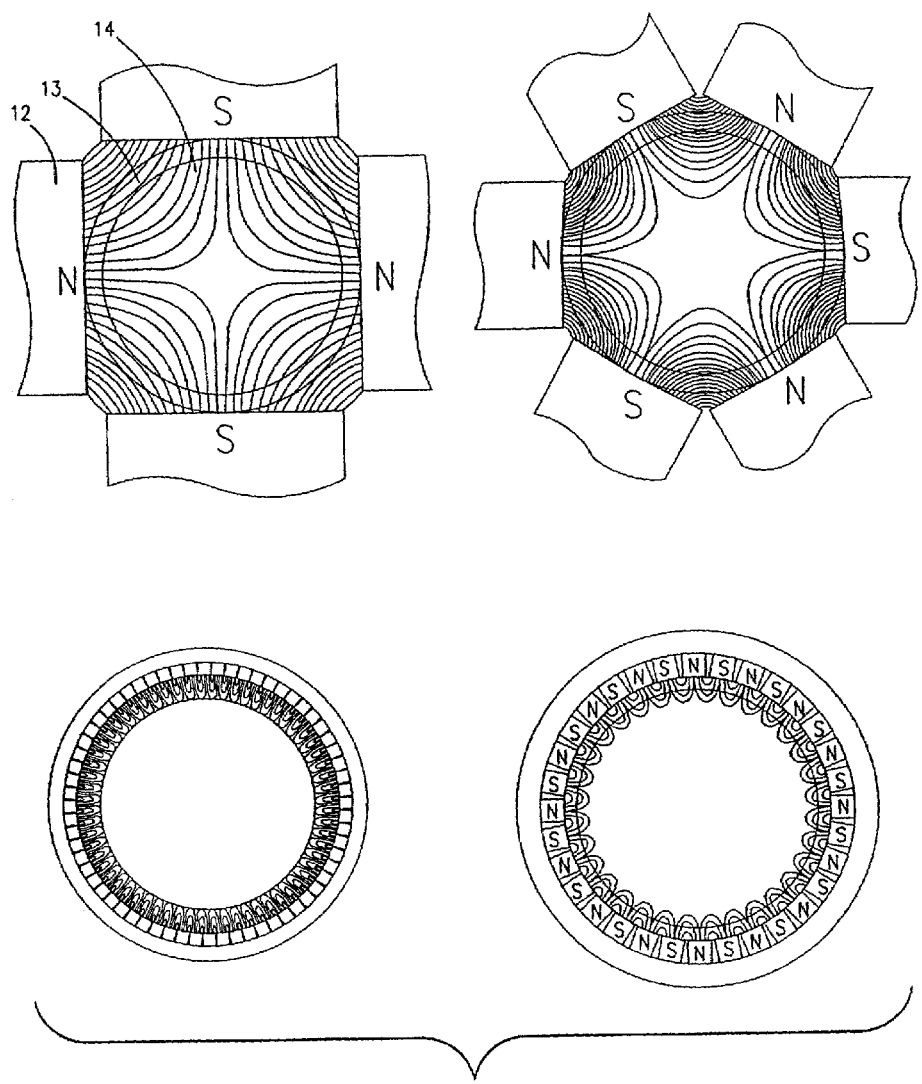
FIG. 1c are enlarged diagrammatic views of the separation systems, shown in FIG. 1b, which have 4, 6, 64 and 32 poles along the vessel wall.
Figure 2A:
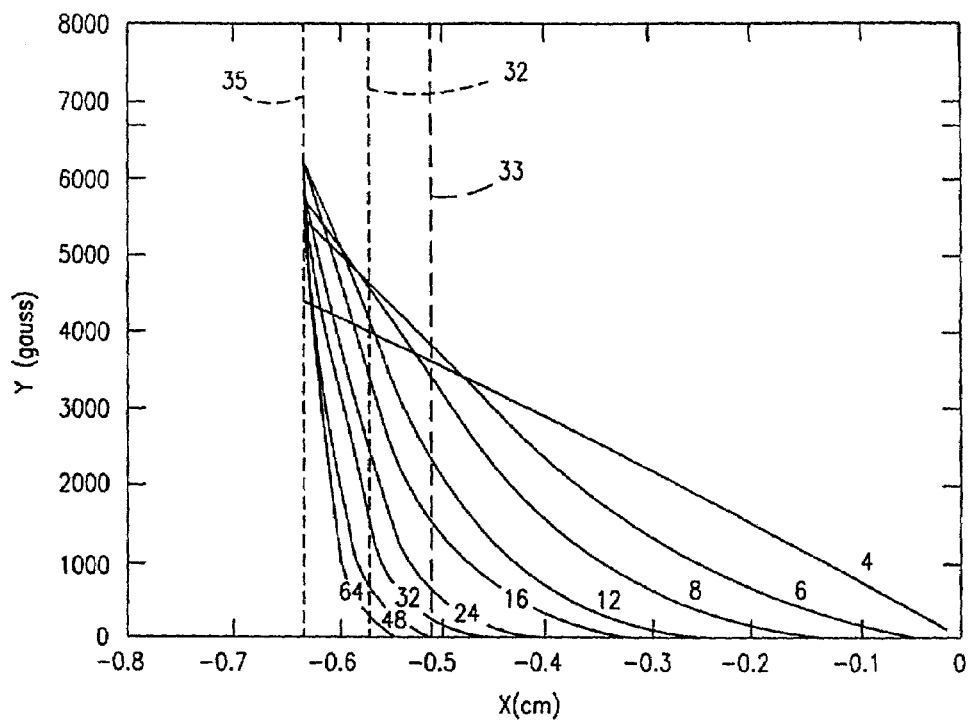
FIGS. 2a and 2b are graphs which plot the magnitude of the magnetic field at different positions on the collection wall.
Figure 2B:
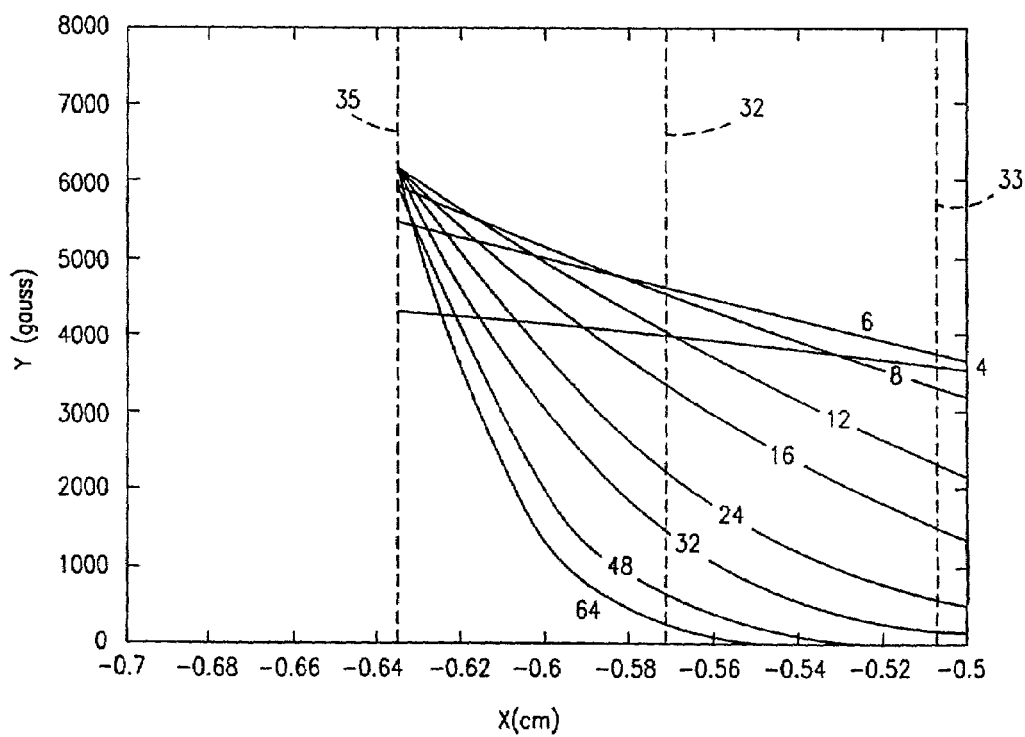
Figure 2C:
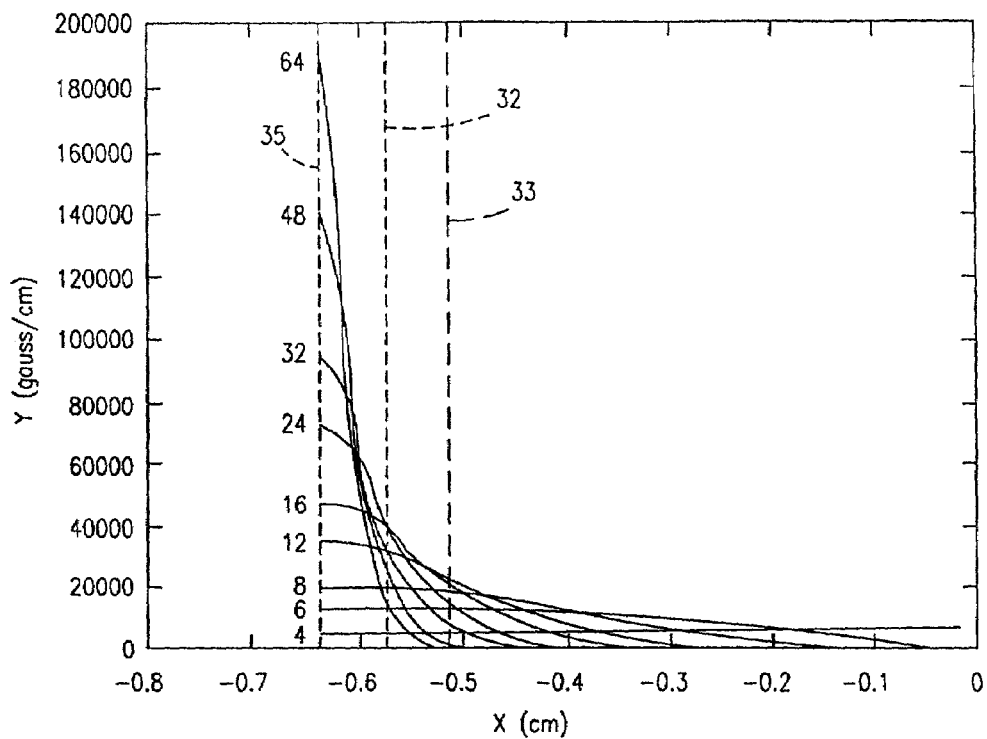
FIGS. 2c, 2d, 2e, and 2f are graphs which plot the magnetic gradient at different positions on the collection wall.
Figure 2D:
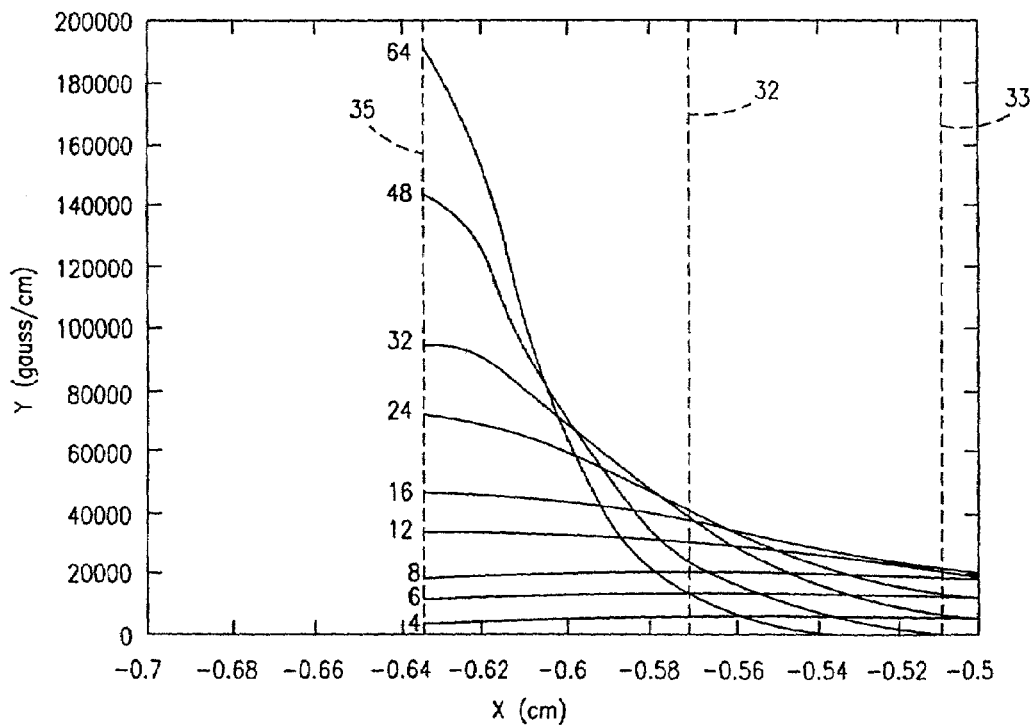
Figure 2E:
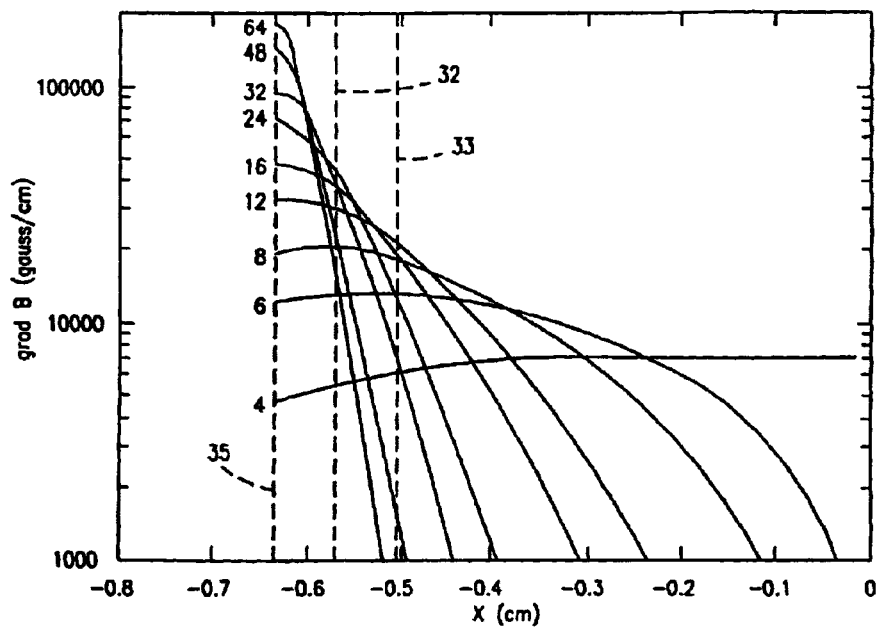
Figure 2F:
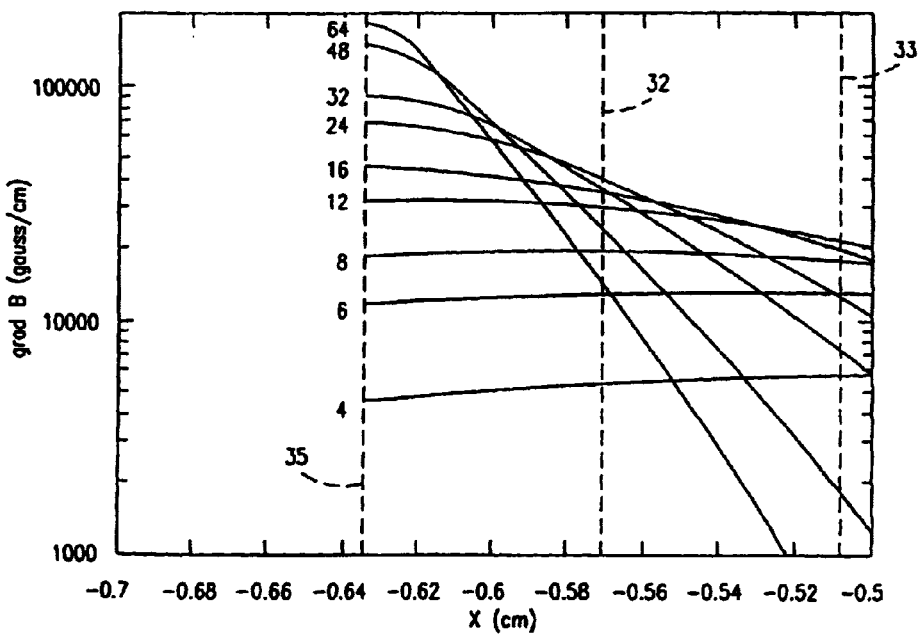

FIGS. 1a and 1b show variation in the number of magnets 12 used while maintaining the container 14 at a fixed diameter and while using magnets 12 where the magnet length equals the width of the pole face. Systems comprising 4, 6, 8, 12, 16, 24, 32, 38 or 64 magnets are shown. FIG. 1a shows that with an increase of the number of magnets 12 around the same separation vessel 10 the overall dimensions of the device become smaller. In FIG. 1b, the generated magnetic field lines are plotted in the container 14 region to illustrate the primary effect of varying the number of magnets 12. The magnetic field (and its gradient) become more closely localized to the pole faces and to the collection surface 32. Note that with an increase in the number of magnets 12 the field gradient at the pole face increases, FIG. 1b. FIG. 1c shows a blow up of the devices with 4, 6, 32 and sixty four magnets 12. While the magnetic field lines are relatively homogeneously distributed in the 4 and 6 magnet configuration, with 32 magnets 12 the spacing between the field lines is more heterogeneous but they just reach beyond the vessel wall 13 and in case of the 64 magnets 12 they remain within the vessel wall 13 (0.636 mm thickness). Note that in the use of round vessels in case of 4 and 6 magnet configurations the vessel 10 actually prevents the target substances from coming to the region were the magnetic gradient is the highest, i.e., at the corners of the magnets 12. From the figures it is clear that separation vessels 10 with shapes which permit the optimal usage of the gradients for a particular magnet arrangement can obviously be made. For example in increasing the vessel diameter the curvature between the magnets 12 become smaller and de facto become a flat plate of equivalently spaced magnets 12. A separation vessel 10 which would suit this magnet configuration could be a thin-walled rectangular separation vessel.

In FIGS. 2a–2f, the magnitude of the magnetic field Y (gauss) (FIGS. 2a, 2b) and the magnetic gradient Y (gauss/cm) (FIGS. 2c, 2d, 2e, 2f) is shown for different positions in a separation vessel 10 which is surrounded by either 4, 6, 8, 12, 16, 24, 32, 48 or 64 magnets 12. The center of the separation vessel 10 is indicated as "0" in FIGS. 2a, 2c and 2e. The distance from the center of the separation vessel 10 to the magnet pole piece is −0.635 cm at 35. The position of the collection surface 32 of the vessel wall 13 is indicated in the figure for a wall thickness of 0.635 mm and referred to as "inner" fluid surface at 33 (see FIG. 3). The inner fluid surface 33 and outer fluid radius at the surface 32 define an annular space 31 (see FIG. 3) where the collection process takes place and is explained in more detail below. The magnitude of the magnetic gradient (Y (gauss/cm) at a given position is the most important variable for moving/separating a magnetically labeled target substance. FIGS. 2c, 2d, 2e and 2f clearly illustrate that for the design with the four or six magnets the gradient is relatively constant throughout the vessel, whereas with increasing number of magnets the gradient is clearly a function of the radius with no gradient at the center of the vessel. Further at the pole faces, substantially greater gradients are obtained by increasing the number of magnets. Note the use of even numbers of magnets is important in case the magnets are placed in a circle but in case of a flat arrangement an uneven number can be used. If an odd number of magnets were used in a circular arrangement, two adjacent magnets would have the same direction which would cause a collection aberration. This could be desirable. It is clear from FIGS. 2a–2f that the thinner the wall of the vessel the better magnetically labeled targets substantially can be separated.

From FIGS. 2a–2f several conclusions can be drawn:

(1) using greater numbers of magnet pairs leads to higher gradients;

(2) in the cases of the highest wall gradients, the drop off is very significant;

(3) (2) dictates the use of extremely thin walled vessels; and (4) to take advantage of (1) and (2), a separation vessel must be used which "blocks" out the region in the center of the vessel so as to place material to be separated near the wall.

The magnetic devices described in this invention use devices and collection vessels which take advantages of these discoveries.

In the separation of target biological substances labeled with magnetic colloids, three important features have to be considered:

(1) The ability to move the magnetically labeled targets to the collection surface.

(2) The ability to hold the magnetically labeled targets at the collection surface 32 while some processing is being conducted; and (3) The ability to release the magnetically labeled targets from the collection surface 32 for other processing procedures (once the magnetic means is removed).

The specific design of the magnetic device, of the collection surface 32, and of the collection space 31 is of importance for the time and efficiency of the separation and the holding of the target substances at the collection surface 32. The intrinsic nature of the collection surface 32 is important for the ability to release the magnetically labeled target substances from the collection surface 32 after the magnetic means is removed as well as for the distribution of the magnetically labeled targets over the collection surface 32 in the collection process. For the sake of this discussion, we will consider the magnetic field roles in attracting, binding, and releasing the target substance only.

Figure 3:
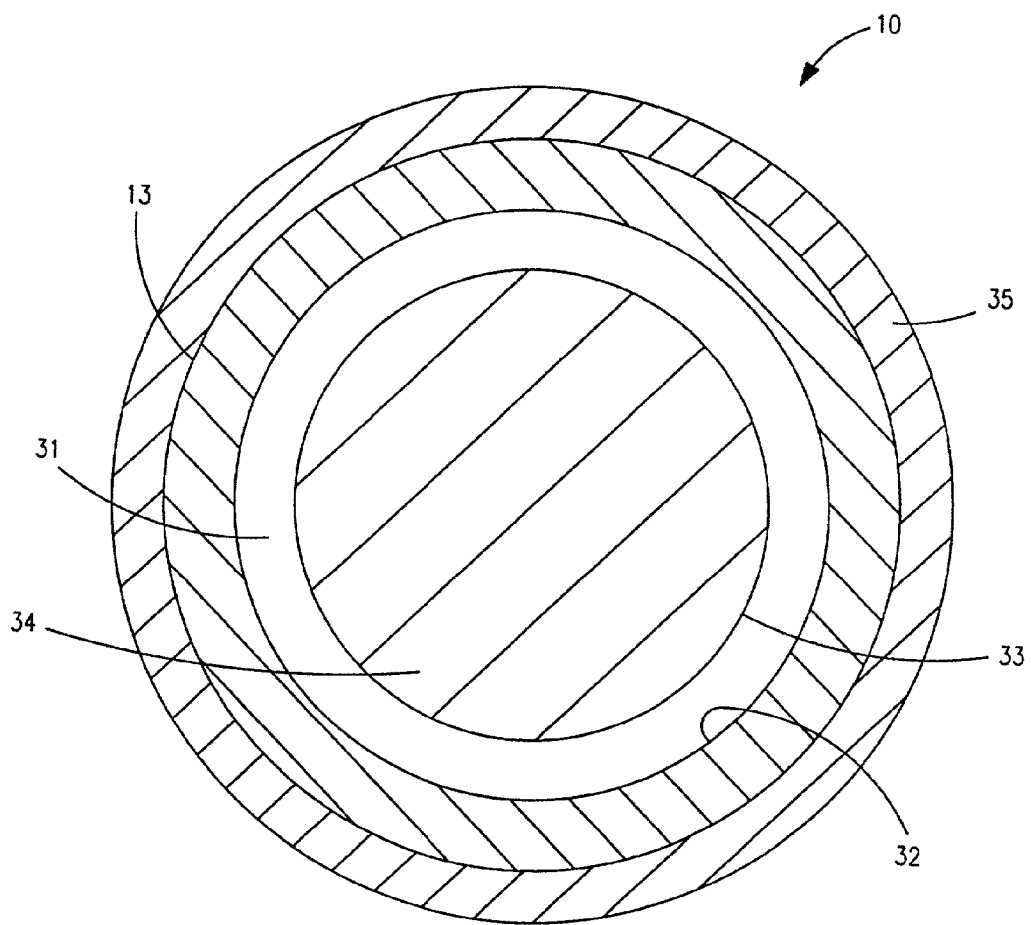
FIG. 3 is a sectional view of a separation vessel.

To determine the optimal configuration of the device, a computer program was written which permits input of many of the relevant variables which can then be tested to quantify the impact of the changes on the effectiveness of the attraction and binding. The program was written for performing separation from annular spaces, as this is a prerequisite. FIG. 3 shows a cross section of an annular collection space 31 within a radial magnetic device and defines relevant components for consideration in performing efficient magnetic separations:

31: annular collection/liquid space.

32: collection surface or inner surface of the separation vessel wall.

33: inner surface of the collection vessel's liquid space.

34: inserted collection activator, a region where no collection is taking place either by placing a physical obstruction such as a non magnetic cylinder, a plunger, a sprayer, or a spinner, examples defined more completely in FIGS. 7a–7g.

35: magnetic field and field gradient source(s).

As the figures indicate, the liquid space is generally a thin annular space as close to the pole faces as is required to achieve maximized separation. In this case, targets are collected to the inner surface 33 of the separation vessel 10 containing the fluid 76.

In some applications, there is a totally opposite configuration whereby the liquid space and collection area is placed on the outer side of the radially placed magnets to be discussed in more detail below. In that case (the fluid is just outside the magnetic field sources); the collection surface is an inner surface of the fluid space.

Figure 4A:
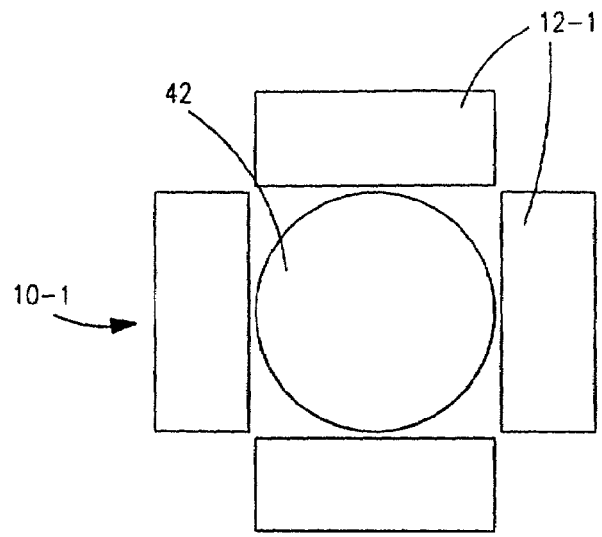
FIGS. 4a through 4d are a diagrammatic views of four magnetic separators embodying the present invention.
Figure 4B:
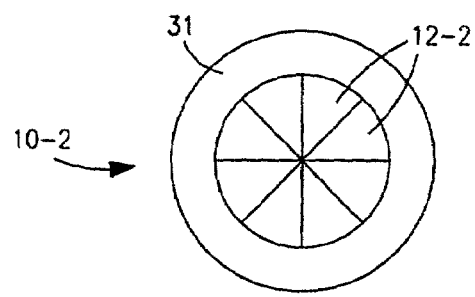
Figure 4C:
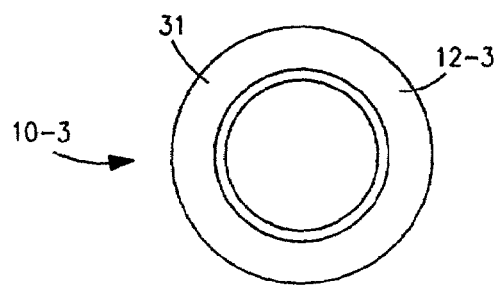
Figure 4D:
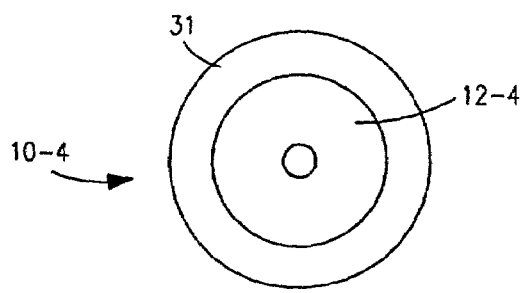

FIGS. 4a–4d show four elemental magnetic designs which can be used to describe the general concepts. In FIG. 4a, magnets 12-1 are placed along the separation vessel 10-1. In FIG. 4b, magnets 12-2 are placed within the separation vessel 10-2. In FIG. 4c, circular magnet plates 12-3 are placed along the separation vessel. In FIG. 4d, circular magnet plates 12-4 are placed within the separation vessel 10-4.

FIG. 4a represents external, conventional magnets 12-1, often rectangular, as shown, but sometimes with some rounding of the magnetic faces, with the magnetization directed toward the central container 42. Only 4 magnets are shown in this example, consistent with U.S. Pat. No. 5,466,574.

FIG. 4b represents a configuration with the magnetic device as the central element surrounded by the annular collection space 31. The magnets 12-2 (six in this example) are analogous to those of FIG. 4a in that the magnetization is radial but the magnets 12-2 are separately aimed away from the center. Their shapes have been adjusted from rectangular to triangular for contiguous packing. Such a configuration of magnets can be located within the core of a plunger as described below.

FIG. 4c represents external circular planar magnets which may be magnetized specially toward the center but are more optimally magnetized parallel to the container and in opposition to neighboring planar magnets which are separated by a paramagnetic spacer ("bucking" arrangement).

FIG. 4d represents planar magnets 12-4 as does FIG. 4c but the magnets 12-4 are internal to the container relevant volume (related to FIG. 4c as FIG. 4b is related to FIG. 4a).

Figure 5A:
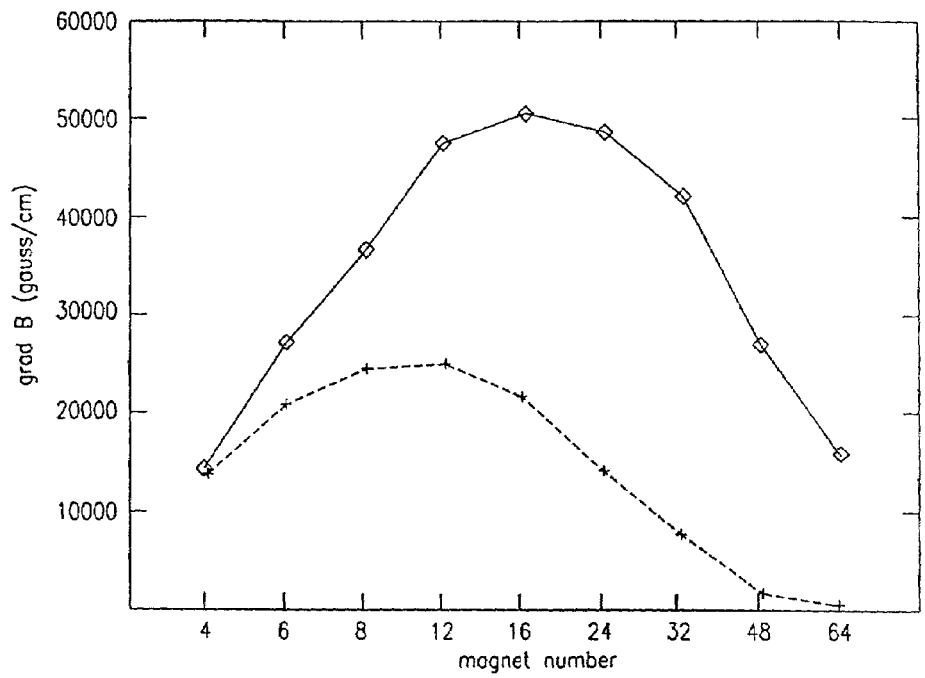
FIGS. 5a and 5b are graphs which show calculations for the effectiveness of magnetic separations.
Figure 5B:
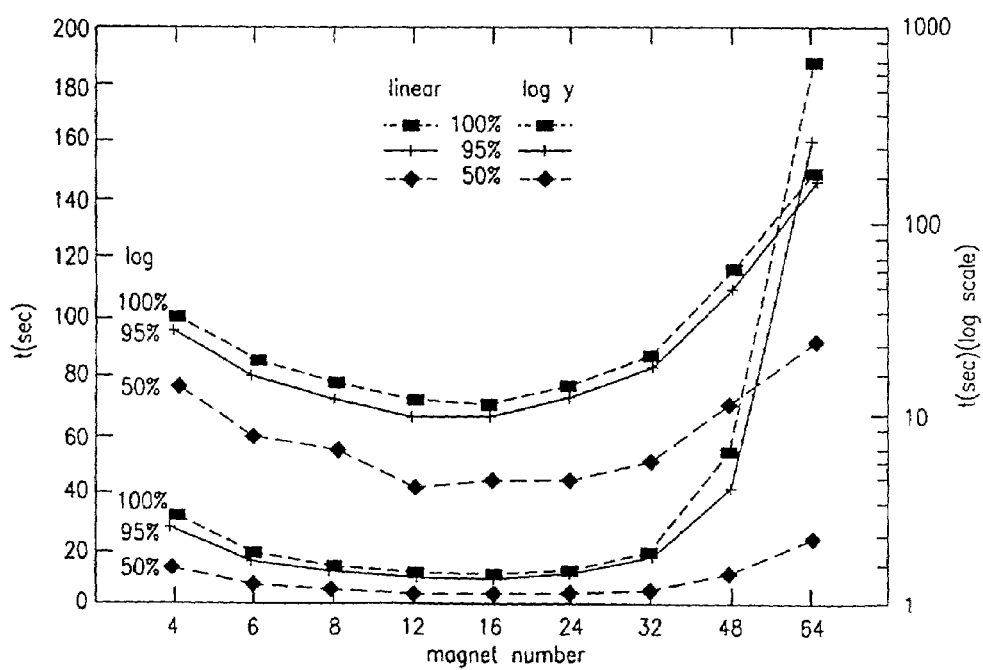

FIGS. 5a, 5b, 6a and 6b show certain plots extracted from computer produced magnetic physics calculation of which the results are tabulated in Tables 2 and 3. The calculations of FIG. 5a assume a separation vessel with an outer diameter of 1.27 cm. The thickness of the wall of the separation vessel is 0.635 nm. The wall of the collection activator is 0.635 mm from the collection vessel wall and the liquid space is thus 0.635 mm. In FIG. 5a, the magnetic field gradient at the collection surface area (outer) and the opposite surface area (inner) is plotted against the number of magnets surrounding the separation vessel. In FIG. 5b, the time to collect 50%, 95% and 100% of the target substances at the collection surface is plotted against the number of magnets surrounding the separation vessel. The left Y axis indicates the time on a linear scale and the right Y axis indicates the time on a logarithmic scale.

Figure 6A:
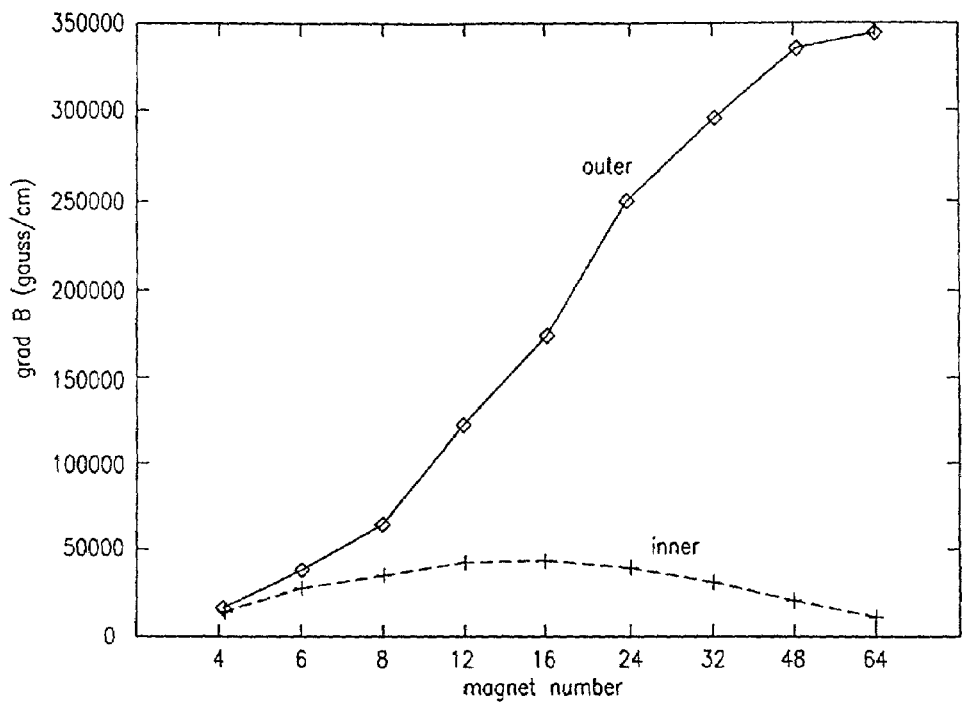
FIGS. 6a and 6b are graphs which show calculations for the effectiveness of magnetic separations for a further separation vessel geometry.
Figure 6B:
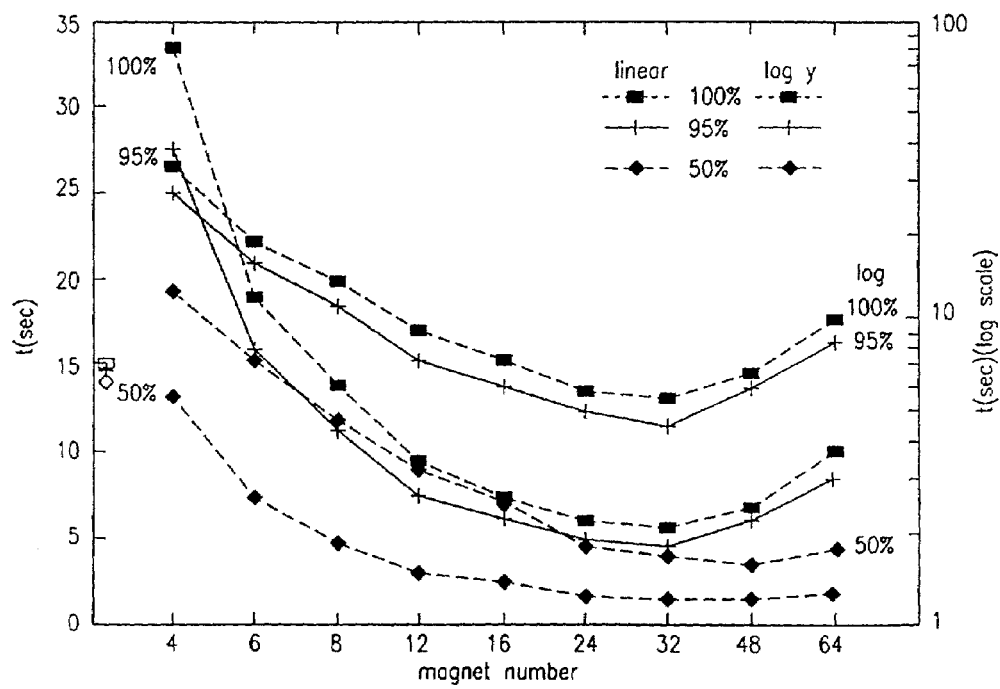

In FIGS. 6a and 6b, the separation vessel has an outer diameter of 1.27 cm, and the thickness of the wall of the separation vessel is 0.1 mm. The wall of the collection activator is 0.635 mm from the collection vessel wall and the liquid space is thus 0.635 mm. In FIG. 6a, the magnetic field gradient at the collection surface area (outer) and the opposite surface area (inner) is plotted against the number of magnets surrounding the separation vessel. In FIG. 6b, the time to collect 50%, 95% and 100% of the target substances at the collection surface is plotted against the number of magnets surrounding the separation vessel. The left Y axis indicates the time on a linear scale and the right Y axis indicates the time on a logarithmic scale.

The calculations are specifically related to the first case in FIGS. 4a through 4d (FIG. 4a) when the magnetic device surrounds the separation chamber but the conclusions drawn will be generalized and associated with the following cases (4b, 4c, 4d) as well.

The tables show several calculated results of interest including the time required to collect certain percentages of the target substance if they are assumed to begin with a random distribution in the fluid volume where they initially exist. Times to collect 50%, 95% and 100% of the cells at the collection surface are included in the table. Also given are the maximum and minimum magnetic field values and gradient values on the chamber inner surface wall which is denoted as the fluid outer surface area or collection surface area (2 in FIG. 3) and on the fluid inner surface area or the surface opposite or most distant from the collection surface (3 in FIG. 3). Such magnetic information explains to some extent the variation in the reported times for collection and also gives the strength of the binding force at the surface (the maximum "outer" gradient value).

TABLE 2

Value of B and ∇B at relevant radius of annular collection vessel in multipole magnetic devices and corresponding collection times.

Collection vessel outer diameter: 1.27 cm.
Collection vessel wall thickness: 0.635 mm.
Collection surface radius: 0.571 cm.
Collection activator radius: 0.508 cm.
Liquid space radius: 0.635 mm.
The number of magnets (Mag num) listed in the left column of the table shows the maximum magnetic field at the magnet pole face (Bmax), the largest (B(max)), and smallest (B(min)) value of the magnetic field at either the collection surface area (outer) or the inner edge of the collection space (inner). The largest (∇B(max)), and smallest (∇B(min) value of the field gradient at the respective positions and the time required to collect 50%, 95% and 100% of the target cells randomly located in the fluid.

| Mag num | Bmax (g) | Time to collect: | | | Along fluid inner or outer surface | | | | surface pos. radius* (cm.) |
|---|---|---|---|---|---|---|---|---|---|
| | | 50% (sec) | 95% (sec) | 100% (sec) | B(min) (g) | B(max) (g) | ∇B(min) (g/cm) | ∇B(max) (g/cm) | |
| 4 | 12500 | 14.1 | 27.7 | 31.8 | 6640 | 7090 | 10200 | 14300 | 0.571 -outer |
| | | | | | 5970 | 6220 | 10800 | 13300 | 0.508 -inner |
| 6 | 10100 | 7.72 | 16.0 | 18.8 | 5730 | 6440 | 17200 | 27200 | 0.571 -outer |
| | | | | | 4650 | 4930 | 16800 | 21100 | 0.508 -inner |

TABLE 2-continued

Value of B and ∇B at relevant radius of annular collection vessel in multipole magnetic devices and corresponding collection times.

Collection vessel outer diameter: 1.27 cm.
Collection vessel wall thickness: 0.635 mm.
Collection surface radius: 0.571 cm.
Collection activator radius: 0.508 cm.
Liquid space radius: 0.635 mm.
The number of magnets (Mag num) listed in the left column of the table shows the maximum magnetic field at the magnet pole face (Bmax), the largest (B(max)), and smallest (B(min)) value of the magnetic field at either the collection surface area (outer) or the inner edge of the collection space (inner). The largest (∇B(max)), and smallest (∇B(min) value of the field gradient at the respective positions and the time required to collect 50%, 95% and 100% of the target cells randomly located in the fluid.

| | | Time to collect: | | | Along fluid inner or outer surface | | | | surface pos. |
|---|---|---|---|---|---|---|---|---|---|
| Mag num | Bmax (g) | 50% (sec) | 95% (sec) | 100% (sec) | B(min) (g) | B(max) (g) | ∇B(min) (g/cm) | ∇B(max) (g/cm) | radius* (cm.) |
| 8 | 8890 | 6.59 | 12.3 | 14.7 | 5130 | 5830 | 23100 | 36900 | 0.571 -outer |
| | | | | | 3720 | 3920 | 20600 | 24700 | 0.508 -inner |
| 12 | 7610 | 4.26 | 9.98 | 11.7 | 4190 | 4690 | 32400 | 47500 | 0.571 -outer |
| | | | | | 2410 | 2480 | 22900 | 25200 | 0.508 -inner |
| 16 | 7030 | 4.69 | 10.0 | 11.2 | 3440 | 3760 | 38500 | 50800 | 0.571 -outer |
| | | | | | 1560 | 1580 | 21100 | 22100 | 0.508 -inner |
| 24 | 6510 | 4.70 | 12.5 | 13.6 | 2320 | 2420 | 42600 | 48700 | 0.571 -outer |
| | | | | | 646 | 651 | 13900 | 14000 | 0.508 -outer |
| 32 | 6280 | 5.82 | 17.2 | 19.8 | 1540 | 1570 | 39500 | 42100 | 0.571 -outer |
| | | | | | 266 | 267 | 7830 | 7870 | 0.508 -inner |
| 48 | 6030 | 12.3 | 43.3 | 55.9 | 671 | 679 | 26700 | 27300 | 0.571 -outer |
| | | | | | 45 | 45 | 2020 | 2030 | 0.508 -inner |
| 64 | 5960 | 24.8 | 162 | 189 | 290 | 293 | 15600 | 15800 | 0.571 -outer |
| | | | | | 8 | 8 | 458 | 462 | 0.508 -inner | units (CGS): g: Gauss; g/cm: Gauss per cm; sec.: seconds

Mag num: number of magnets

Bmax: the maximum field value at a magnet surface.

time to collect: time required for given percentage of randomly positioned cells to reach the collection surface.

B(min), B(max): minimum and maximum field values on a surface outer: collection surface area inner: opposite surface of the collection activator dB(min), dB(max): minimum and maximum field gradient values on a surface (inner or outer)

Surface position radius: fluid space inner or outer surface

The two key results (time to collect and outer gradient strength) presented in the table are plotted in FIGS. 5*a* and 5*b* for the data of Table 2 and FIGS. 6*a* and 6*b* for the data of Table 3. The results of FIGS. 5*a*, 5*b*, 6*a* and 6*b* are depicted for a container of the diameter represented in FIGS. 1*a*, 1*b* and 1*c*, (1.27 cm o. d.) and either a 0.635 mm wall thickness (Table 2 data) or a smaller, 0.1 mm, wall thickness (Table 3 data). It is noted that the total volume in the annular collection space 31 is approximately equal in the two cases in Tables 2 and 3. The ∇B at the collection surface (holding force) and the collection times are, however, significantly different. This is due to bringing the collection surface 32 and collection activator 34 closer to the pole faces.

For either case the goal is to collect and hold target particles on the chamber collection surface. The calculations are based on conventional ferromagnetic and paramagnetic physical principles and on certain selected parameters for magnets, the fluid and target characteristics as well as certain geometrical estimates.

TABLE 3

Value of B and VB at relevant radius of annular collection vessel in multipole magnetic devices and corresponding collection times.

Collection vessel outer diameter: 1.27 cm.
Collection vessel wall thickness: 0.1 mm.
Collection surface radius: 0.625 cm.
Collection activator radius: 0.561 cm.
Liquid space radius: 0.635 mm.
The number of magnets (Mag num) listed in the left column of the table shows the maximum magnetic field at the magnet pole face (Bmax), the largest (B(max)), and smallest (B(min)) value of the magnetic field at either the collection surface area (outer) or the inner edge of the collection space (inner). The largest (VB(max)), and smallest (VB(min)) value of the field gradient at the respective positions and the time required to collect 50%, 95% and 100% of the target cells randomly located in the fluid.

| | | Time to collect: | | | Along fluid inner or outer surface | | | | surface pos. |
|---|---|---|---|---|---|---|---|---|---|
| Mag num | Bmax (g) | 50% (sec) | 95% (sec) | 100% (sec) | B(min) (g) | B(max) (g) | VB(min) (g/cm) | VB(max) (g/cm) | radius (cm.) |
| 4 | 12500 | 13.2 | 27.6 | 33.5 | 7170 | 7910 | 9670 | 15600 | 0.625 -outer |
| | | | | | 6530 | 6950 | 10300 | 14100 | 0.561 -inner |
| 6 | 10100 | 7.47 | 16.1 | 18.9 | 6640 | 8150 | 16600 | 37600 | 0.625 -outer |
| | | | | | 5560 | 6180 | 17200 | 26000 | 0.561 -inner |
| 8 | 8890 | 4.87 | 11.3 | 13.9 | 6370 | 8400 | 23100 | 64300 | 0.625 -outer |
| | | | | | 4890 | 5470 | 22800 | 34300 | 0.561 -inner |
| 12 | 7610 | 3.21 | 7.55 | 9.45 | 6040 | 8640 | 35600 | 122000 | 0.625 -outer |
| | | | | | 3860 | 4250 | 31100 | 42400 | 0.561 -inner |
| 16 | 7030 | 2.61 | 6.18 | 7.55 | 5830 | 8590 | 47700 | 174000 | 0.625 -outer |
| | | | | | 3070 | 3280 | 35600 | 44000 | 0.561 -inner |
| 24 | 6510 | 1.83 | 5.07 | 5.97 | 5470 | 8100 | 71400 | 251000 | 0.625 -outer |
| | | | | | 1920 | 1980 | 36500 | 39900 | 0.561 -inner |
| 32 | 6290 | 1.68 | 4.70 | 5.68 | 5190 | 7470 | 94100 | 296000 | 0.625 -outer |
| | | | | | 1180 | 1200 | 31200 | 32400 | 0.561 -inner |
| 48 | 6110 | 1.53 | 6.07 | 6.84 | 4690 | 6290 | 136000 | 336000 | 0.625 -outer |
| | | | | | 447 | 450 | 18200 | 18400 | 0.561 -inner |
| 64 | 6020 | 1.78 | 8.60 | 10.2 | 4230 | 5310 | 172000 | 346000 | 0.625 -outer |
| | | | | | 168 | 168 | 9240 | 9280 | 0.561 -inner | units (CGS): g: Gauss; g/cm: Gauss per cm; sec.: seconds
Mag num: number of magnets
Bmax: the maximum field value at a magnet surface.
time to collect: time required for given percentage of randomly positioned cells to reach the collection surface.
B(min), B(max): minimum and maximum field values on a surface
outer: collection surface area
inner: opposite surface of the collection activator To create the tabulated data, the calculations were repeated with the same estimates for magnetic sources of increasing numbers of magnets (denoted in Column 1 of table 2 and 3). The absolute values are dependent on the mentioned multiparameter values chosen but the most relevant and most general result is the variation in values from one magnetic number set to the next. As a result, one can roughly estimate for a particular case a result of the kind listed: "for a given type of target, what is the optimal number of magnets to use for chambers of this size." The issues of interest are the variation in the strength of target binding (holding force) and the times of target collection for systems of varying numbers of magnets. FIG. 5a gives the gradient values, i.e. the relevant holding strength, at the collection surface area (outer in FIG. 3) and at the inner edge of the collection space (inner in FIG. 3). The optimal gradient holding strength is shown to occur near a magnet number of 16 and is significantly larger than is obtained for a magnet number of 4 or 6. The effective gradient value is found to fall off if the magnet number is further increased, however, and from the value at the opposite surface farthest from the magnets (inner), one also sees that as the number increases the gradient affecting the movement of the most distant target cells falls off even more rapidly. This is reflected in the "observed" (FIG. 5b) increase in the total collection time as the number of magnets is further increased. The optimal collection time also occurs in the magnet number regime of 12 to 24.

FIGS. 6a and 6b and Table 3 give analogous results with only one geometrical change. The chamber is of the same outer dimension but the wall is thinner. This demonstrates the potential advantage of decreasing the wall thickness once the optimum magnet number has been selected.

In the table and in the plot of FIG. 6a the "outer" gradient is observed to be still increasing as one increases the magnet number to 64 although the gradient at the "inner" surface of the collection space is significantly dropping. This accounts largely for the increase in the collection time. Noted more importantly, the indicated choice of 16 to 32 magnets for this case produces significant improvements in both collection time and holding strength.

The simplest variation to discuss is the dimensions of the collection vessel or "tube". The above cases on included plots of the variation of the relevant field gradients and estimated collection times for targets of specific properties. The variation in the number of magnets is thereby shown to effect the performance of the target process. Additionally the variation in the wall thickness is also shown to affect the performance. An unlimited number of additional tables could be constructed for such different tubes of different diameter and wall thickness. The number of magnets chosen will differ for different size chambers as will be seen for the 48 magnet choice described for the larger diameter tubes presented in FIGS. 7a–7g.

Not shown in the tables and figures is a set of parameters which is used in the computer simulations which involves the target cell properties and their fluid environment. A particular set of parameters was chosen for demonstration of the results but are not described. The times listed would vary for targets of a different kind, but the main object of the stated result is the relative value and importance of varying the number of magnets. For example, the time required to collect 95% of the target cells of the properties assumed in those calculations may differ by a factor of 10 (or ⅒) for another target parameter but the optimal choice for the magnet number would be the same. Similarly using stronger (or weaker) magnets would alter magnitudes of the results but the magnet number choice would remain the same.

As mentioned above, the calculations discussed are specifically related to the first case in FIGS. 4a through 4-d (FIG. 4a) but the conclusions drawn should be considered more general and associated with the following cases (4b, 4c, 4d) as well. Similar calculations and results have been obtained for the case where multipole radial magnets 12 are placed within a annular collection space (FIG. 4b) i.e. magnets internal rather than external. Less quantitative approximations were made for the planar magnet cases but the approximate solution can be confidently accepted. A similar number of magnets 12 is desirable for the same fluid diameter to maximize the available gradient at the collection surface 32 and to provide a sufficient gradient at the opposite surface to provide acceptable complete collection times. A rough, conservative approximation for any of the sets is easily stated to be the greatest possible minimization of the magnet to collection surface distance maximizes the holding strength; to ensure collection of the most distance targets (at or near the opposite surface) the period of the magnet positions should not be less than twice the distance from the magnet face to the opposite surface.

Although the above teaches that an annular space is the optimal design for a magnetic separator having multiple pairs of magnets, the actual volume which can be separated is relatively small. Flowing the suspension containing the target entities through the vessel has the disadvantage that the targets will preferentially collect at the beginning of the vessel resulting in an inhomogeneous collection over the collection surface and potentially clogging up the system. An alternative approach, which is another objective of this invention is to bring the suspension close to the collection surface 32 by other means.

FIGS. 7a to 7g show four variations accomplishing the latter which exploits the magnetic devices and concepts outlined in FIG. 4a and in FIGS. 1a–1c, 5a–5b and 6a–6b. The enlarged gradient produced near the collection surface may be exploited by having a container where as noted separation takes place in a narrow annulus or what can be referred as a "separation" annulus. This can be accomplished by employing a separation cylinder FIG. 7a, a "plunger" which moves through the center FIG. 7c, a "sprayer" FIG. 7g, or a "spinner" which brings cells into the annulus FIG. 7e.

Figure 7A:
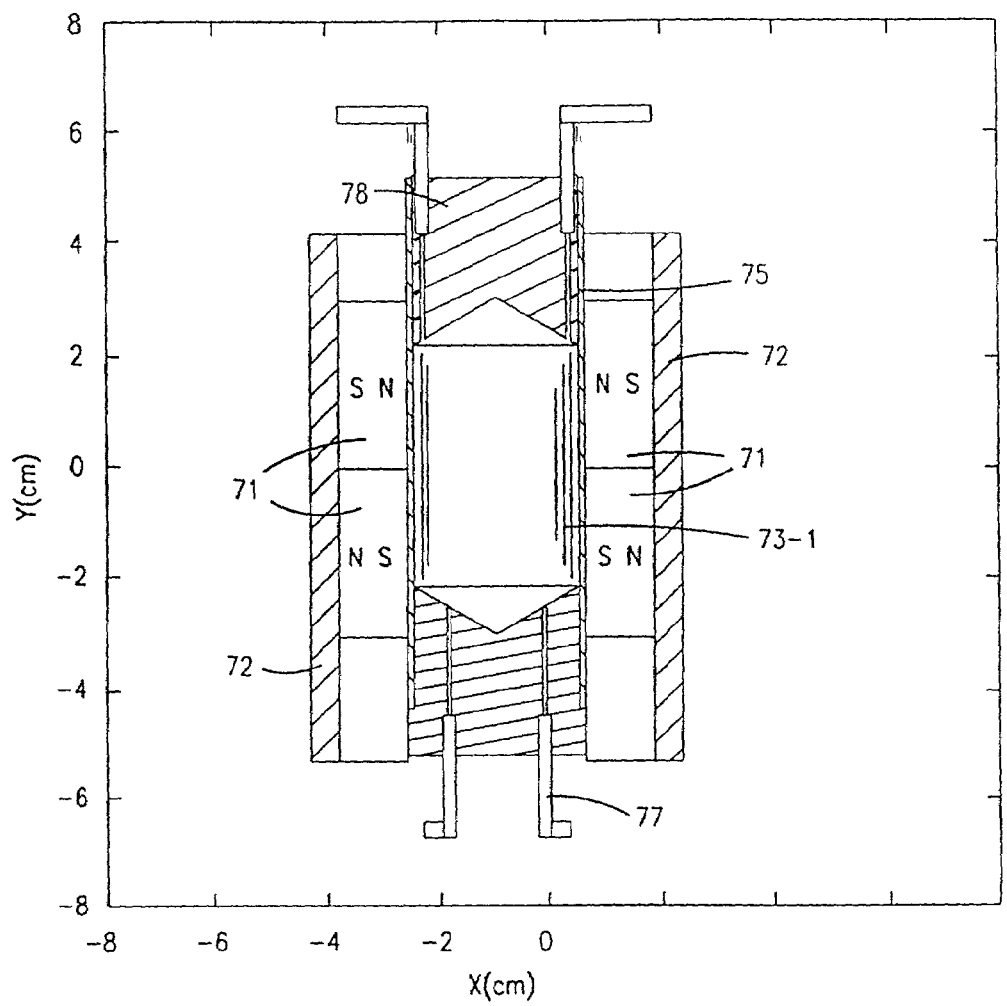
FIG. 7a is a diagrammatic longitudinal section of a first embodiment of a magnetic separation system embodying the present invention.
Figure 7B:
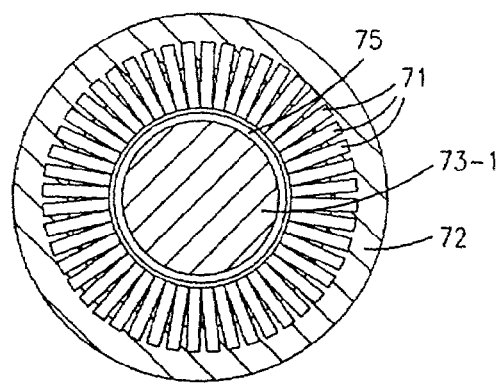
FIG. 7b is a diagrammatic transverse cross section of the first embodiment.
Figure 7C:
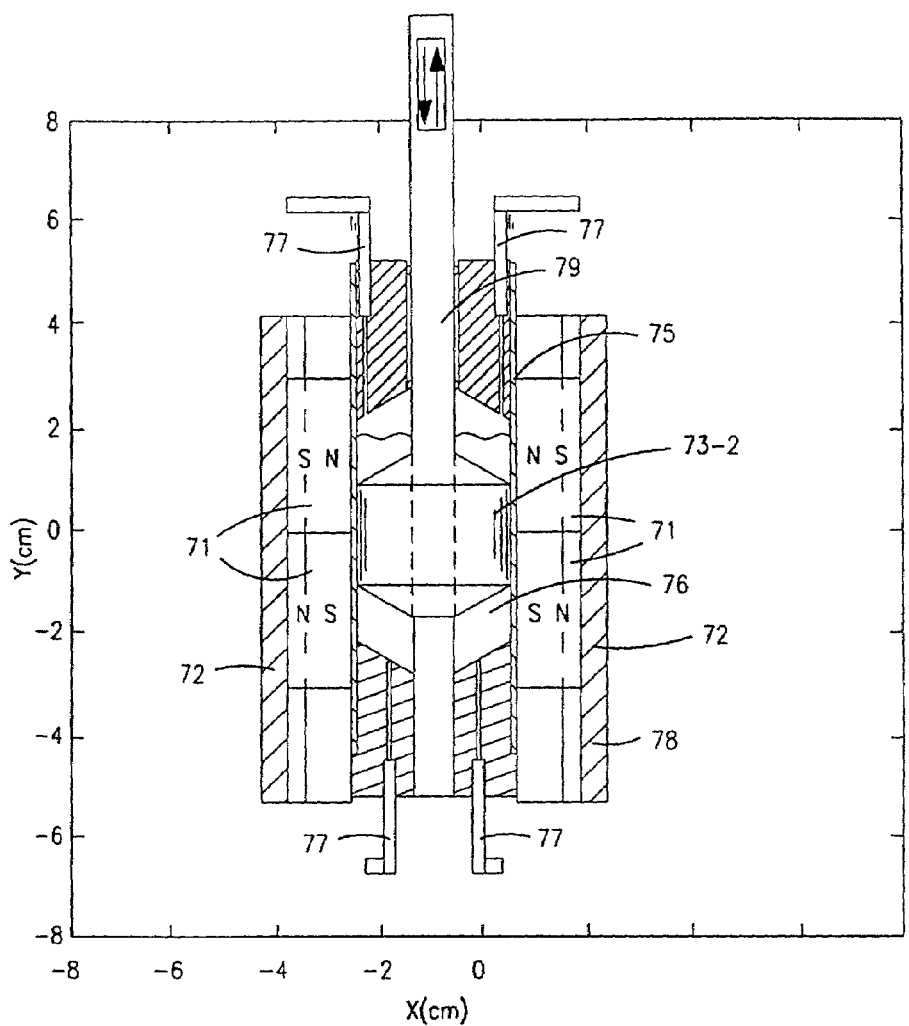
FIG. 7c is a diagrammatic view in longitudinal section of a second embodiment of a magnetic separation system embodying the present invention and comprising a plunger.
Figure 7D:
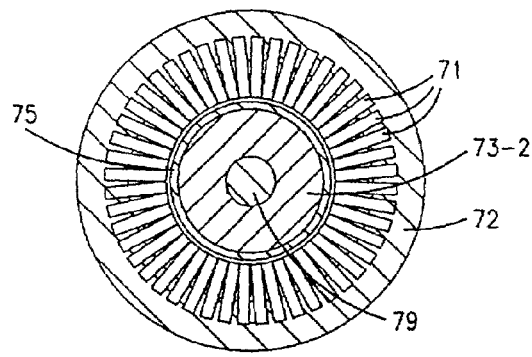
FIG. 7d is a diagrammatic transverse cross section of the second embodiment.

FIG. 7a depicts a presently produced magnetic device of a size determined by an existing container tube of usable wall thickness. The yoke 72 is 1.246 inches=3.165 cm and the wall thickness is 0.46 mm(average). Although not included here the appropriate tables and figures analogous to Tables 2 and 3 (FIGS. 5 and 6) for this size were produced. The analogous result indicates the use of 48 magnets for this (size and thickness) yoke container. The magnets 71 are 2 mm wide and are almost touching each other (2Π×3.175 (r)/48 (#magnets)=2.07 mm period). The baffle 73-1 excludes the fluid 76 from being farther than a fixed separation of 0.5 mm from the container (separation vessel) 75 collection surface. The time for total collection of all target cells analogous to those implicitly considered in Table 2 would be comparable to the optimal time in the table (~10 sec). The total volume in the container 75 shown would be approximately 2 milliliters. This volume could effectively be increased by increasing the size of the container 75 if compatible with other application conditions or one could flow continual amounts of fluid though the container 75, trapping the targets while non-target material passed through. This direct input flow will result in trapping of the target particles and outflow of the rest of the fluid if the "internal lifetime" of the target cells is long enough to ensure their collection and if accompanying elements of the process (for example, fluid turbulence) do not obstruct the collection or impose forced release of trapped targets. Fluid flows into and out of container 75 through tubes 77. Even when successful a problem with such procedure is a non-uniformity in the entrapment of the targets as they deposit most frequently in the entrance position and are undesirable localized there. FIGS. 7b, 7c and 7d show adaptations which have been tested and constructed in varying degrees (FIG. 7b is presently constructed in the geometrical shape shown) and which are considered procedural structures included in this invention as relevant exploitation of the external field gradient intensification.

FIG. 7c shows a "plunger" 73-2 of external diameter equal to the separation vessel 75 of FIG. 7a. The plunger 73-2 can be swept up and down to ensure that all parts of the fluid 76 spend a selected time within the annular space where separation will take place. The total volume in the annular separation space at any given time is ~1 ml but the total container volume is 15 ml, a substantial increase from FIG. 7a. Furthermore, the plunger motion results in a spreading of the collection areas fairly uniformly over the inner chamber wall which is strongly required in many high density target operations. Furthermore, if one desires to further increase the workable volume, one can increase the geometrical size as mentioned in the FIG. 7a description, but even more effectively so that volumes in the liter range can be treated.

Furthermore, the "painting" of the wall by movement of the plunger 73-2 with precise control to eliminate scraping (achievable by conventional engineering construction techniques being used), can be later reversed if desired by application of the same plunger motion at different speeds and/or with a variance to achieve turbulent flow by removal of the magnetic field sources.

Some of the above advantages can be obtained comparably with two other "painting" structures which compete in advantageous usefulness in various applications. FIG. 7g shows a fluid "sprayer" 73-4 version which permits even larger volume of fluid 76 in the same container although it generally requires also some initial inclusion of an external presence of an initial external fluid before the "spraying" inside the fluid 76 begins. The fluid 76 being investigated is slowly flowed in from the hollow drive shaft 80 through tubes 67 which "spray" it against the wall 33 with sufficiently slow rates that target materials are successfully separated and held on the container wall 33. The functioning of the spraying is further illustrated in FIG. 7g. The sprayer outlets 66 are rotated and raised as the fluid input continues, producing a "painting" of the wall which is spread over the region covered in the motion. The analogy to a spray painting is quite accurate in this case. This "painting" of the targets on the wall is effectively performed by fixing the output openings at a distance equal or comparable to that of the inner cylinder in FIG. 7a or the plunger surface in FIG. 7b (0.5 mm). By limiting the inflow rate attraction of the target cells to the collection surface during the lifetime spent within the annular separation space, separation can be accomplished before the outflow pushes them away from the wall to a larger distance where the magnetic force essentially vanishes. As considered for FIG. 7e, the "painting" of the wall 33 by movement of the sprayer edges with precise control to eliminate scraping can be later undone if desired by application of the same sprayer with new fluid, at different speeds and/or with a variance or removal of the magnetic field sources. The sprayer can be used to turbulently release the targets in subsequent desirable fluid procedures.

Figure 7E:
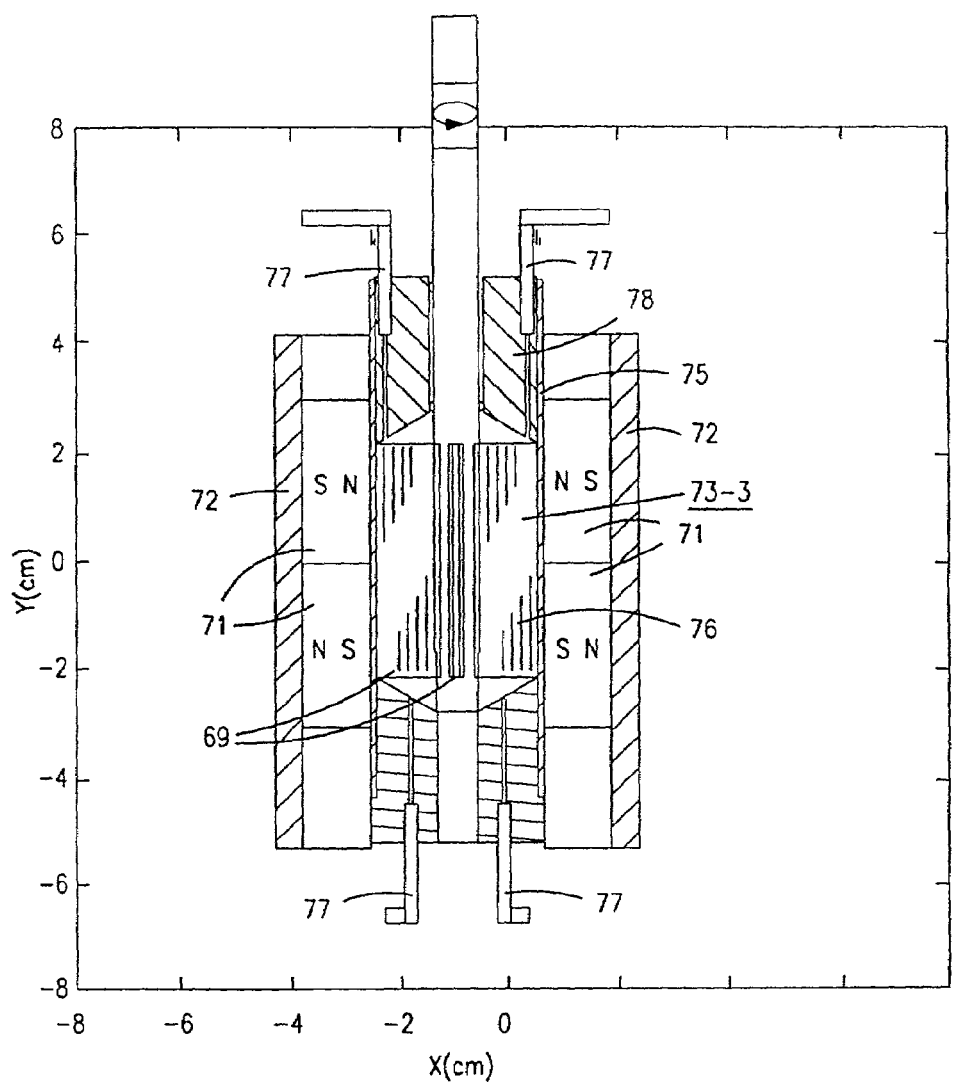
FIG. 7e is a diagrammatic longitudinal section of a third embodiment of a magnetic separation system embodying the present invention and comprising a stirrer.
Figure 7F:
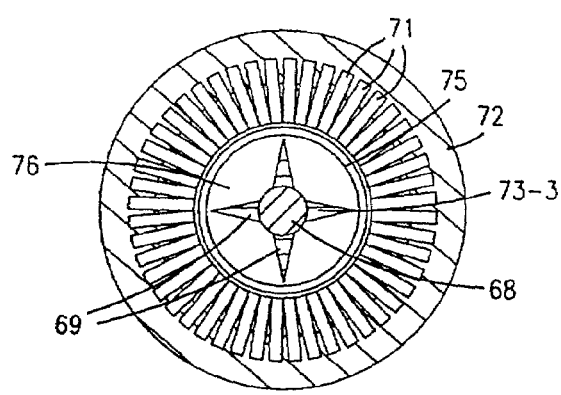
FIG. 7f is a diagrammatic transverse cross section of the third embodiment.
Figure 7G:
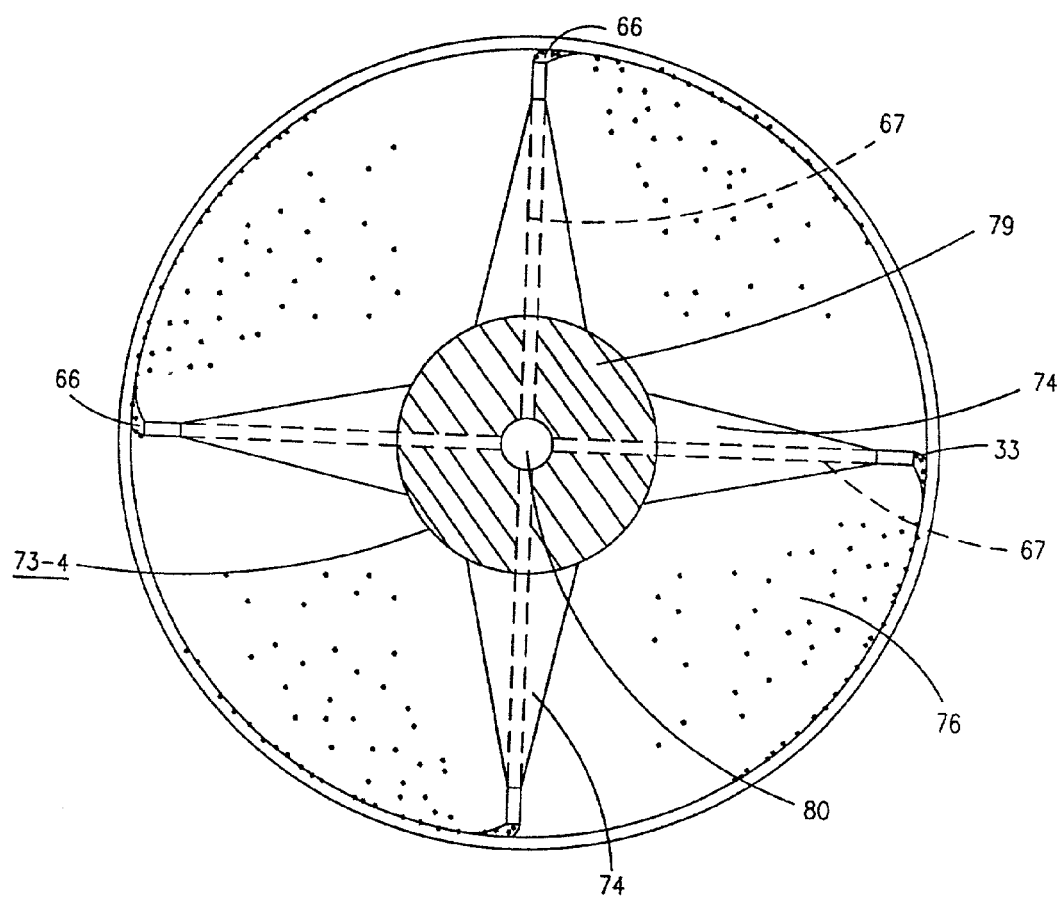
FIG. 7g is a diagrammatic transverse cross section of a fourth embodiment of a magnetic separation system embodying the present invention and comprising a sprayer, where the sprayer may be used in place of the stirrer of the third embodiment.

FIGS. 7e and 7f show a fluid "stirrer" mechanism which is operated after the fluid of interest is deposited in the container. The total volume is comparable to FIG. 7c and is similarly expandable. The "painting" of the targets on the wall is performed here by rotating the indicated stirrer 73-3 having blades 69 which are mounted on a rotatable shaft 68 and whose edges approach the annular separation space. After a certain amount of time and number of rotations, all of the target substances will have passed within the annular space and will be attracted and held. It is required that the stirring be slow enough such that the average time spent in this vicinity is long enough to produce collection of any target particle and that resultant turbulence will not produce removal. Faster "stirring" may be used subsequently for other purposes. As considered for FIG. 7c, the "painting" of the wall by movement of the stirrer edges with precise control to eliminate scraping can be later undone if desired by application of the same stirrer motion at different speeds and/or with a variance or removal of the magnetic field sources. The stirrer 73-3 can be used to turbulently release the targets in subsequent desirable fluid procedures.

FIG. 7g shows a sprayer 73-4 having a hollow shaft 79 with blade 74 which may be rotated to deposit the targets on the wall of the chamber. In FIG. 7g, the sprayer 73-4 has a hollow shaft 79 with a central bore 80 for introducing the fluid of interest 76 containing the targets into the annular space at 66 adjoining the inner surface 33 of the collection vessel by way of radial passages 67 in the blades 74.

Figure 8B:
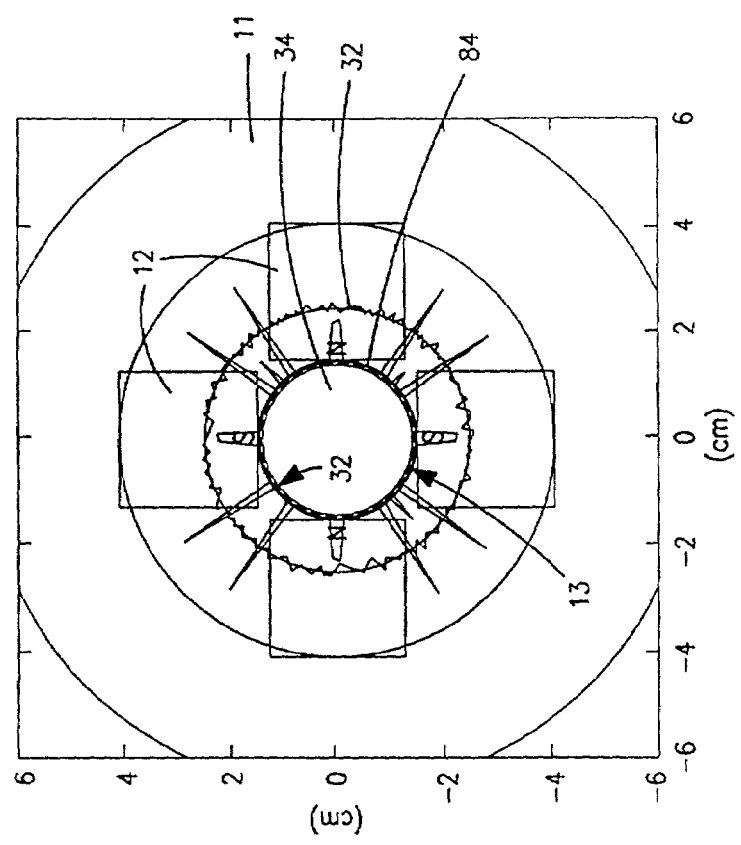
FIG. 8b is a schematic cross section of a 4-pole separation system having a collection surface which allows slipping of the colloidal magnetic particles and the magnetically-labeled target substances along the surfaces.
Figure 8A:
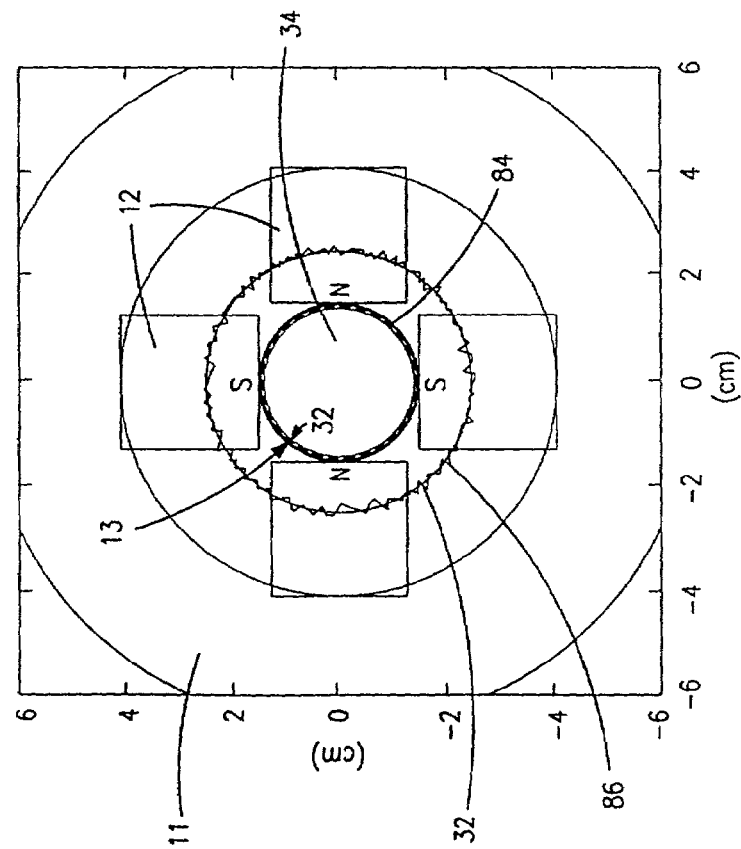
FIG. 8a is a schematic cross section of a 4-pole separation system having a non-slip collection surface and showing the distribution of target substances along the collection surface area.

Colloidal magnetic particles and or magnetically labeled targets present in the separation vessel 75 move according to the magnetic field lines to the collection surface. After they reach the collection surface the position where a target collects may change in a lateral direction if there is a gradient of higher magnitude nearby. Recall that earlier it was noted that there is periodic variation of the gradients at the collection surface due to the flat pole pieces employed in these devices. In FIGS. 8a and 8b, 4 opposing magnets 12 are placed along the vessel as described in U.S. Pat. No. 5,466,574 and in FIGS. 8c and 8d, 48 magnets 12 are placed along the vessel wall. FIG. 8a shows a collection vessel surrounded by four magnets, and shows the distribution of target substances along the collection surface made from a material which prevents slipping of colloidal magnetic particles and magnetically labeled target substances. The collection vessel has a diameter of 1.246 inches (3.165 cm) and a wall thickness of 0.46 mm with 4 or 48 magnets along the vessel wall. The collection activator, excludes the fluid from being farther than 0.5 mm from collection surface area.

A histogram 86 is plotted along the collection surface indicating the distribution of the particles along the collection surface 32 at the time they hit the collection surface 32. As can be seen in FIG. 8a the distribution of the target substance 84 along the collection surface 32 is quite homogenous. Depending on the surface of the container the target substances 84 may not be electrostatically or chemically bound to the collection surface 32 or trapped by "holes" or "curbs" in the collection surface 32. FIG. 8b shows a collection vessel surrounded by four magnets, and shows the distribution of target substances along the collection surface made from a material which allows the colloidal magnetic particles and magnetically labeled target substances to slip along the collection surface area. In the case when the collection surface 32 is "slippery" the magnetically labeled targets will move along the collection surface 32 if there is a magnetic gradient component in a parallel plane direction. The perpendicular component is obviously canceled by the wall. Roughly speaking, the final location will often be near the highest magnetic force which is near the edges of the magnetic sources as is illustrated by the histogram 86 in FIG. 8b.

Figure 8C:
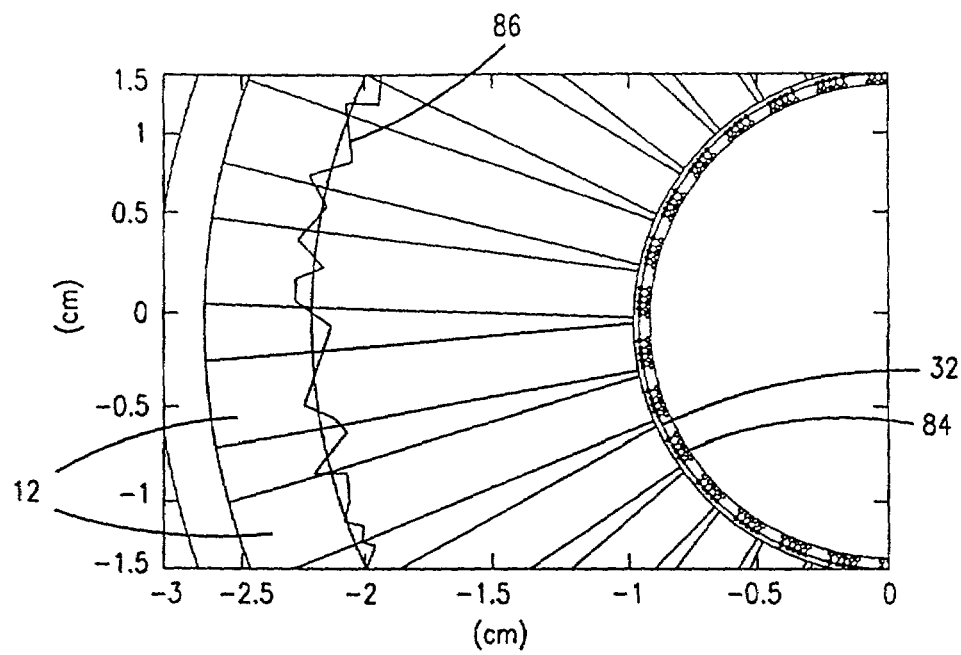
FIG. 8c is a fragmentary schematic cross section of a 48-pole separation system having a non-slip collection surface and showing the distribution of target substances along the collection surface area.
Figure 8D:
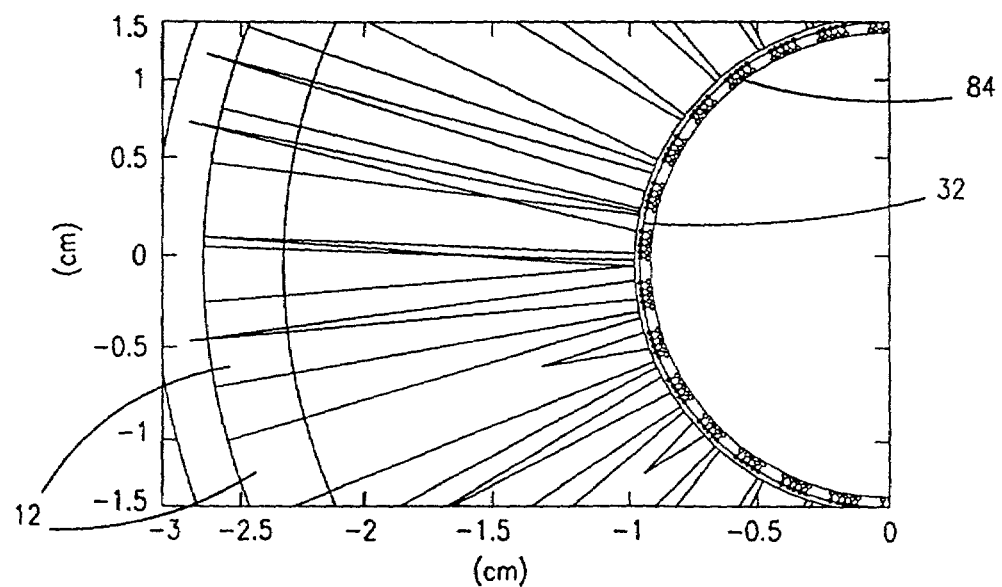
FIG. 8d is a schematic cross section of a 48-pole separation system having a collection surface which allows slipping of the colloidal magnetic particles and the magnetically-labeled target substances along the surface and showing the distribution of target substances along the collection surface area.

A homogenous distribution over the collection surface 32 is often preferable. For example, in the case where the targets are cells, one would prefer a monolayer of cells in order to avoid entrapment of non target cells by piles of targets, to avoid cell damage, to avoid cell clumping, and to increase the capacity per collection surface area. By increasing the number of magnets 12 along the collection surface 32 the magnetically labeled targets will be more evenly spread over the collection surface 32 even if the surface cell motion is permitted (As shown in FIG. 8c, there are many more peaks and in this sense less concentration of the cells). By changing the surface properties, the nature of the collection surface 32, one can also decrease the ability of the cells to move along the surface. 32 This is in fact easier to achieve for the larger magnet number device; the strength of the gradient moving the targets 84 along the surface 32 significantly decreases although this is not apparent in the result expressed in FIG. 8d. FIG. 8d shows a collection vessel surrounded by 48 magnets 12 and shows the distribution of target substances 84 along the collection surface 32 made from a material which allows the colloidal magnetic particles and magnetically labeled target substances 84 to slip along the collection surface area 32. One has to remember, however, that even in this case, any excess, non-magnetic bonding which inhibits the relatively weak planar motion and yields a smoother final target 84 distribution, can not be so strong that it may later not be overcome by slight manipulations needed and used to re-suspend the targets 84 after the magnetic means have been removed.

Removal of the magnetic means enables the particles to be resuspended. The removal of the magnetic means may be in association with modification of the flow pattern provided by the sprayer 74 or stirrer 69, or by movement of the plunger 73. If the pole faces of the magnetic means are displaced longitudinally of the collection surface 32, the magnetic field tends to apply shear forces on the particles in the direction of relative movement. To avoid such forces, the pole faces may be displaced outwardly away from the collection surface 32, so that the magnetic field gradient is reduced sufficiently to afford resuspension in a direction generally perpendicular to the collection surface 32. To this end the magnetic device may be separated into two or more parts which may be separated perpendicularly to the collection surface 32, reducing the magnetic field gradient without applying shear forces to the particles adhered to the surface 32.

An alternate method to control lateral slide of targets and to specifically position them on the collection surface 32 and also have the ability to facilitate the release of the cells from this surface 32 is to have a collection surface 32 which has localized and defined gradients superimposed on the collection gradients. This can be achieved with a microscale pattern on the collection surface 32 made of ferromagnetic material, such as nickel, shaped and sized appropriately to suit the biological target substance 84 of interest. Such patterns can be made by standard lithographic or electroplating processes. The ferromagnetic material acts as a local field intensifier. A target first moves towards the collection surface 32 under influence of the external magnetic means and when close to the collection surface 32 comes under the influence of the local intensifier whose field strength dominates the local target attraction and binding. A description of this dual use of magnetic gradients is described in U.S. patent application Ser. No. 08/867,009, now U.S. Pat. No. 5,985,153.

Figure 9A:
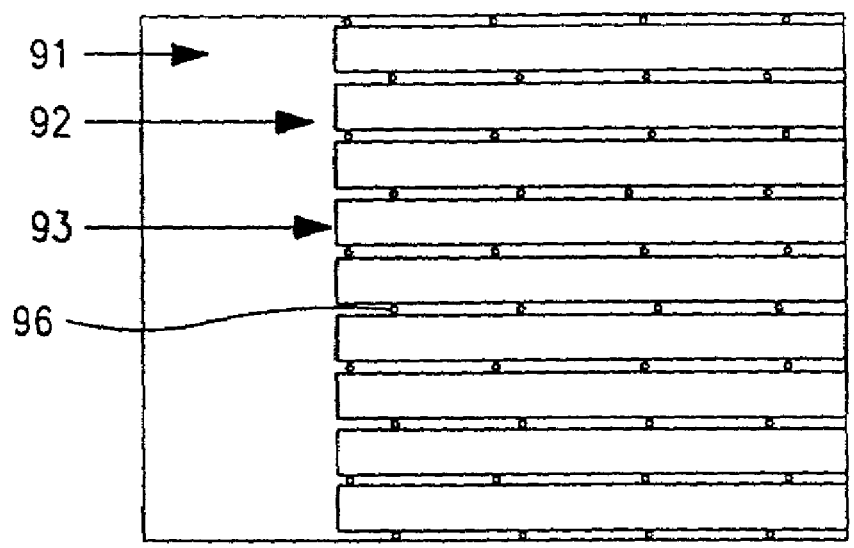
FIG. 9a illustrates a glass substrate having ferromagnetic microscale pattern spaced from one edge for use in the present invention.

An example of such a pattern is shown in FIG. 9a. Nickel was deposited by standard lithographic techniques on a glass surface 91, the pattern of deposition were lines 92 with a width of 23 um 93 and a spacing of 7 um. The thickness of the Nickel was 0.5 μm (0.0005 mm). This collection surface was placed in a magnetic field and a fluid containing magnetic colloidal particles 96 with an average size of 150 nm was placed on the surface. All the particles 96 are collected between the lines 92 as is recorded in FIG. 9a. In the figure no particles are present on the glass surface 91 portion with no Nickel lines 92. All the particles 96 are present between the lines 92 or protruding slightly over the lines 92 where the line structures start.

Figure 9B:
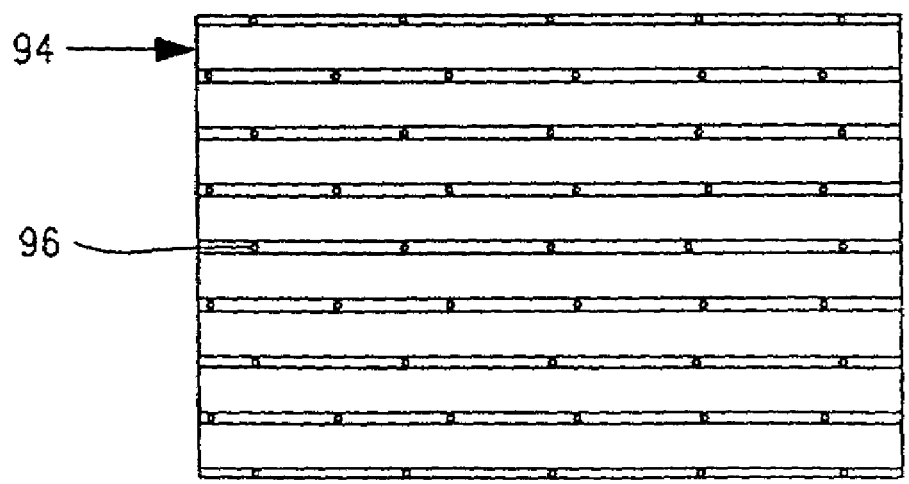
FIG. 9b illustrates a glass substrate similar to the substrate in FIG. 9a having a ferromagnetic microscale pattern extending from edge to edge.

In FIG. 9b a similar collection surface was used but now the fluid placed on the collection surface was peripheral blood incubated with colloidal magnetic particles labeled with an antibody specific for leukocytes. As can be seen in the figure, the magnetically labeled cells 94 in the blood, line up nicely between the lines. It is obvious to one skilled in the art that different ferromagnetic patterns on the collection surface will not only provide a means to homogeneously distribute the targets but, in addition, will substantially increase the holding force. This will permit faster initial collection of fluid flowing along the collection wall and, further, will allow more stringent fluid flows in subsequent processes (for example, "washes"). Another utility of the nickel or comparable metal pattern is that, when connected to a power supply, the nickel could easily be positively or negatively charged. Electrical charge of the nickel pattern will further add to the holding of the negatively charged targets and can later be used to facilitate target release by reversing the charge (positive to negative).

Figure 9C:
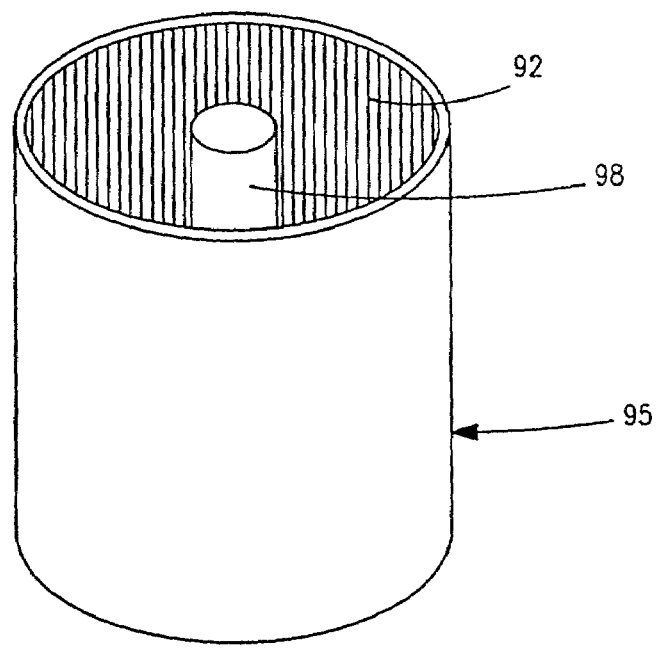
FIG. 9c is a diagrammatic perspective view of a collection vessel with a collection surface containing a ferromagnetic pattern of Nickel lines.
Figure 9D:
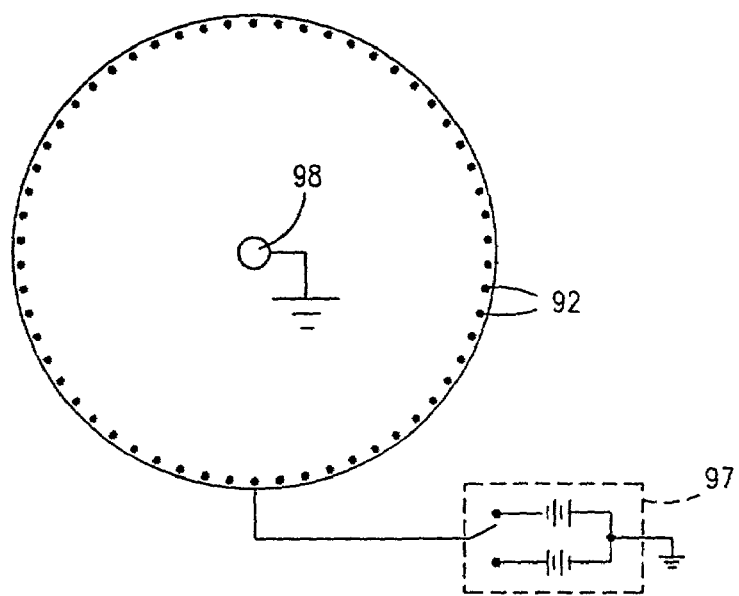
FIG. 9d is a diagrammatic view in cross section of the vessel of FIG. 9c illustrating connections between the vessel and a power supply.

In FIGS. 9c and 9d, schematic drawings of the collection vessel 95 are shown in which the collection wall 99 has a collection surface with the Nickel lines 92 as shown in FIGS. 9a and 9b. The insulated Nickel lines are connected to a power supply 97 and a rod 98 is shown in the center of the vessel. The rod may be contained within the plunger driver shown in FIG. 7b which then serves as the electrical ground of the chamber.

DESCRIPTION OF PREFERRED EMBODIMENTS

Preferred embodiments of the present invention and methods will now be described in detail with reference to the drawings.

The magnetic separation apparatus and methods of the present invention have particular utility in various laboratory and clinical procedures involving biospecific affinity reactions. In such procedures, particles are used which are at once magnetically responsive and colloidal (i.e., particles which are paramagnetic and capable of remaining in suspension in a non-magnetic test medium), and which comprise a receptor capable of binding the substance of interest in the test sample. In the present method, after the receptor binds the target substance, the magnetic separator removes the magnetic particles from the test medium via HGMS.

Such biospecific affinity reactions may be employed in testing biological samples for the determination of a wide range of target substances, representative of which are cells, cell components, cell subpopulations (both eukaryotic and prokaryotic), bacteria, parasites, antigens, specific antibodies, specific biological factors, such as vitamins, viruses and specific nucleic acid sequences, as in the case of gene probe analysis. Thus, the magnetic separation apparatus and methods of the invention may be used to carry out cell separations for the analysis or isolation of cells including, by way of example: T-cells, B-cells, dendritic cells, hematopoietic progenitors, mesenchymal progenitor; non hematopoietic tumor cells from bone marrow or peripheral blood (leukopheresis products).

Similarly, the present magnetic separation apparatus and method may be used in bacterial or parasite separation or analysis, including the separation of various bacteria and parasites from fecal matter, urine, sludge's, slurries and water (e.g., ground water or streams). The present invention may also be used in separating various bacteria in food products (liquids to solids) sputum and urine.

The preferred magnetic particles for use in carrying out this invention are particles that behave as true colloids. Such particles are characterized by their sub-micron particle size, which is generally less than about 200 nanometers (nm.) (0.20 microns) and their stability to gravitational separation from solution for extended periods of time. Suitable materials are composed of a crystalline core of paramagnetic material surrounded by molecules which may be physically absorbed or covalently attached to the magnetic core and which confer stabilizing colloidal properties. The size of the colloidal particles is sufficiently small that they do not contain a complete magnetic domain, and their Brownian energy exceeds their magnetic moment. As a consequence, North Pole, South Pole alignment and subsequent mutual attraction/repulsion of these colloidal magnetic particles does not appear to occur even in moderately strong magnetic fields, which contributes to their solution stability. Accordingly, colloidal magnetic particles are not readily separable from solution as such even with powerful electromagnets, but instead require a relatively high gradient magnetic field to be generated within the test medium in which the particles are suspended in order to achieve separation of the discrete particles.

Magnetic particles having the above-described properties can be prepared as described in U.S. Pat. Nos. 4,795,698; 5,597,531; and/or 5,698,271.

FIG. 7a shows a rather direct exploitation of the maximized magnet number usage of the high magnetic field gradients available within 0.5 mm of the outer barrier of the fluid (the tube inner wall). The fluid occupancy is within the outer chamber and outside an inner cylinder which has the same center as the outer chamber and an outer diameter a predetermined distance (0.5 mm in this example) from the outer chamber inner wall. The total volume of fluid in the chamber is only the inner chamber height (4.26 cm) times the outer circumference ($\Pi \times 3.07 = 9.6$ cm) times the fluid layer thickness (0.05 cm): 2.05 cm$^3$ (ml). This volume can be increased proportionately by increasing the chamber inner height or diameter. Moving to 10 ml would not be too costly but it would be difficult to push the device into the liter (1000 ml) range. One could, however, flow a large volume of liquid through the chamber resulting in the extraction of the target cells from the flow through fluid caused by deposition on the chamber surface if the flow through time was long enough to result in the collection and slow enough that the flow through turbulence did not dislodge targets from their entrapment. The volume that can be dealt with is proportional to the permitted target deposition density on the chamber surface. However, there will be a major peak in this density at the fluid entrance position and there will be a decline in this density toward the output. In fact this decline must be quite rapid to ensure that some cells do not leak out. This may or may not be of some inconvenience in later analysis but the primary difficulty is the eventual obstruction caused by the maximal build-up at the entrance position which will limit the maximum input possible.

Removal of the target cells from the inner chamber may be accomplished by subsequent rapid flow of a desired fluid through the chamber area to dislodge the target particles through their turbulence; this turbulence and the necessary fluid input required are minimized by first removing the chamber from the magnet container, or removing the magnet pole faces from the outside of the collection surface. Alternative removal and additional target particle treatment capabilities would be permitted by additional device construction properties which provide for the initial (before release of the target particles from the chamber wall) removal of the inner cylinder with sufficient position control that the removal of the cylinder did not dislodge the target cells from the chamber wall. This capability is present in the embodiment shown in FIG. 7c.

FIG. 7c shows a currently used example of the "plunger" version of the several original, here proposed exploitation of the maximized magnet number. In the figure, inlets and outlets are indicated by which fluids 77 can be introduced or removed. After introduction of the suspension incubated with the target specific magnetic colloids the plunger 73 is moved, and the suspension now will be forced into the separation space between the plunger 73 and the collection surface. The particles free in solution and the magnetically labeled targets will now be homogeneously distributed along the entire collection surface while maintaining the high magnetic gradient. The speed with which the plunger 73 can be moved depends on the holding force and the degree of turbulence caused hydrodynamic forces.

For part of the chamber height, as in the first example, the fluid occupancy is within the outer chamber and outside an inner cylinder which has the same center as the outer chamber and an outer diameter a predetermined distance (0.5 mm in this example) from the outer chamber inner wall. The total volume of fluid in this portion the chamber is only the inner chamber height (2 cm) times the outer circumference ($\Pi \times 3.07 = 9.64$ cm) times the fluid layer thickness (0.05 cm): 0.96 cm$^3 \approx 1$ cm$^3$ (ml). This volume can be increased or decreased proportionately by changing the inner cylinder (plunger 73) vertical size as long as it remains small compared to the chamber inner height. But the total fluid volume is considerably larger since it includes the rest of the chamber volume above and below the present location of the plunger 73. This volume is the rest of the height (4.46 −2 cm) times the total plunger 73 cross-sectional area (7.4 cm$^2$) minus the relatively small cross sectional area of the plunger driver (0.78 cm$^2$). The total volume is approximately 15 ml for the existing example shown and this can be increased quite easily to the liter range by increasing the chamber height and/or width. The volume dependence is essentially that of an empty cylinder. Only the target particles in the small outer plunger area are rapidly attracted but by moving the plunger 73 up and/or down the total volume is flowed through the narrow plunger-inner chamber wall 0.5 mm slot ($\approx 1$ cm$^2$ cross sectional area) and all target cells are placed in the proper position for the necessary time. The time a target particle spends in this region close to the trapping surface must be long enough to ensure entrapment. In addition, the rate of the flow caused by the plunger motion must (initially) be slow enough that turbulence does not cause removal of trapped target particles. For example, if the required time were that of the minimum time predicted in table I (~10 sec for 100% entrapment of target cells), the maximum flow rate would have to be 2 cm/10 sec=0.2 cm/sec=2 mm/sec. This corresponds to a volume flow of 1 cm$^2 \times 0.2$ cm/sec=0.2 ml/sec requiring a total of approximately 15/0.2=75 sec of total plunger movement. If this speed were found to be causing dislodgment of trapped targets or if the true required time was longer, a longer plunger movement time would be executed for this purpose. If the real required time was longer, a longer plunger movement time could be used but in some cases it might be preferred to perform repetitious plunger motions to produce the same result. A primary element of the device design is the accurate control of the plunger 73 position relative to the outer chamber; the accuracy of the "0.5 mm" separation position is kept accurate (presently within 20%) and in particular there is no scraping of the chamber wall by the plunger 73.

After the separation has taken place, the suspension can be removed and replaced by washing buffers and, if desired, the separation can be repeated to further reduce non target substances. After separation and washing is complete, the vessel 75 can be taken out of the magnetic field and the targets can be resuspended from the wall of the vessel 75. Removal of the target cells from the inner chamber may be accomplished by subsequent rapid movement of the plunger 73, most often after the original fluid was removed and replaced. The resultant flow of desired fluid through the chamber area will dislodge the target particles through their turbulence; the turbulence required is minimized by first removing the chamber from the magnet container. Alternative removal and additional target particle treatment capabilities are permitted by existing device construction properties. The plunger 73 can be removed without scraping of the chamber wall and the vessel 75 can be removed from the magnetic container for various customary fluid chamber usage's (for example centrifuging).

One important consequence of the devices and concepts disclosed here is that by creating very high magnetic gradients external to the separation vessel 75 and by designing the vessel to take advantage of those gradients, targets weakly magnetic or cells with low density magnetic labeling can effectively be separated. A lower level of magnetic labeling creates many obvious advantages particularly for post separation processing.

EXAMPLE 1

The ability to detect and enumerate epithelial cell derived tumor cells in peripheral blood opens new perspectives for the early diagnosis and monitoring of patients with cancer. The finding that such cells appear in the blood in tumors still thought to be localized to the primary site and the finding that the number of these cells per blood volume is correlatable with the activity of the disease or the tumor cell load opens new perspectives in the management of patient with cancer (PNAS, 1998). The frequency of these cells is, however, extremely low and for screening purposes a sensitivity of 1 tumor cell/1–10 ml of blood is required with a high degree of precision. Requirements for the technique used to prepare the blood sample for analysis are volume reduction, reproducible recovery of tumor cells of at least 75% and a low carry over of non target cells (<0.01%) and other non target substances. With the use of biospecific colloidal magnetic particles in concert with the high gradient open field magnetic devices, these goals can be achieved even in cases were the density of the ligand on the target is low.

The monoclonal antibodies specific for epithelial cell adhesion molecule (EPCAM) such as GA73.3, berEP-4, KS1, HEA125 or MJ37 are broadly reactive with tissue of epithelial cell origin. The GA73.3 antibody was coupled to colloidal magnetic particles. EPCAM coated Ferrofluid (200 ul) and 5 ml of wash and dilution buffer was added to 10 ml of blood and the sample incubated for 15 minutes (Immunicon, Huntingdon Valley, Pa.). The sample can then be introduced through the inlet 7 in the plunger version of the magnetic separation system shown in FIG. 7b. The plunger/drive can now be moved through the separation vessel. After introduction of the suspension incubated with the target specific magnetic colloids the plunger is moved, the sample now will be forced into the separation space between the plunger and the collection surface. The particles free in solution and the magnetically labeled epithelial cells will now be homogeneously distributed along the entire collection surface.

The time a magnetically labeled epithelial cell spends in the separation region must be long enough to ensure entrapment. The rate of the flow caused by the plunger motion must (initially) be slow enough that turbulence does not cause removal of trapped target particles. After the separation has taken place, the sample devoid of epithelial cells is removed and is replaced by a washing buffer through the inlets and outlets illustrated in FIG. 7b.

The separation can be repeated to further reduce non target substances. After separation and washing is complete, the vessel can to be taken out of the magnetic field, or the magnetic field may be removed from the collection wall of the vessel by displacing the magnets radially outward or by having a hinged yoke that is easily opened, and the epithelial cells can be resuspended from the wall of the vessel.

Removal of the epithelial cells from the collection wall may be accomplished by subsequent rapid movement of the plunger in a the washing buffer. The resultant flow of the wash buffer through the chamber area will dislodge the free particles and magnetically labeled epithelial cells through their turbulence. Further increases in the purity of the epithelial cells can be obtained by placing the collection vessel back in the magnetic field and repeating the process described above. For this particular example, it is important to reduce the sample volume, using the plunger shown in FIG. 7b or a plunger which occupies a larger percentage of the liquid space as the means to resuspend the cells collected at the wall. The volume of the wash buffer can be reduced since it is only required to wet the collection surface. The wash buffer can also contain agents which permeabilize the epithelial cells to enable the detection of receptors which are expressed within the cytoplasm or the nucleus. At the stage where the volume can be reduced to less then 1 ml, the captured cells can be resuspended in a buffer containing the receptors used to discriminate between the captured cells. For example fluorescently labeled monoclonal antibodies such as phycoerythrin (PE) conjugated anti-cytokeratin (AE1, CAM5.2 Mab) and Peridinin Chlorophyll Protein (PerCP) labeled CD45. After incubation for 15 minutes, 2 ml of buffer is added and the cell suspension is magnetically separated. After discarding the nonseparated suspension containing excess fluorescent antibodies, the collected cells are resuspended in a buffer volume compatible with the analytical means used.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A magnetic separation apparatus for separating magnetically responsive particles from a non-magnetic test medium, the apparatus comprising a non-magnetic container having an interior surface, magnetic means having a gap receiving the container, said magnetic means generating a magnetic field gradient within the container in which the magnetic field strength within the container is stronger in the test medium along the interior surface of the container than in the test medium more distant from the interior surface and is operative upon the magnetically responsive particles within the test medium to attract the magnetically responsive particles toward the interior surface of the container and cause such particles to be attracted to the interior surface; and a non-magnetic plunger operable to be displaced into said container to provide an annular space within said interior surface into which said non-magnetic test medium may pass.

2. The magnetic separation apparatus of claim 1 wherein said container comprises:

an elongated hollow cylindrical passage having an inlet for introducing the non-magnetic test medium into one end of the passage and an outlet for discharging test medium from the opposite end of the passage, said interior surface being located between said inlet and said outlet.

3. The magnetic separation apparatus of claim 2 wherein said hollow cylindrical passage is configured for conducting a flow of fluid therealong in a direction parallel to the longitudinal axis of the passage from said inlet to said outlet.

4. The magnetic separation apparatus of claim 2 wherein said gap of the magnetic means comprises a plurality of pole faces each disposed at an operative position exteriorly of said container adjacent said interior surface, said pole faces being disposed circumferentially of said cylindrical axis of the passage, At least one of said pole faces being mounted for displacement radially outward from the axis of the passage to afford reduction of the magnetic field strength within the container, and thereby afford reduction of the attraction of said particles to said interior surface adjacent the operative position of said at least one pole face.

5. A magnetic separation apparatus for separating magnetically responsive particles from a non-magnetic test medium comprising a non-magnetic container having an interior surface, magnetic means generating a magnetic field gradient within the container in which the magnetic field strength within the container is stronger in the test medium along the interior surface of the container than in the test medium more distant from the interior surface and is operative upon the magnetically responsive particles within the test medium to attract the magnetically responsive particles toward the interior surface of the container and cause such particles to be adhered to the interior surface, and a non-magnetic deflector comprising a plunger having an outside configuration similar to said interior surface and dimensions less than the inside dimensions of said interior surface to provide an elongated annular space along the length of the interior surface and operable to deflect magnetically responsive particles into said narrow annular space immediately adjoining said interior surface along which said non-magnetic test medium passes.

6. A magnetic separation apparatus according to claim 5 wherein said plunger is operable to be displaced in said container to confront said interior surface and spaced therefrom to form said annular space into which said non-magnetic test medium may pass.

7. A magnetic separation apparatus according to claim 6 wherein said annular space is optimized to facilitate test reactions and collection of the magnetically responsive particles within said annular space.

8. A magnetic separation sapparatus according to claim 5 wherein said container interior surface is carried by said plunger, and said magnetic means is mounted in said plunger and comprises pole faces directed toward said interior surface.

9. A magnetic separation apparatus according to claim 5 wherein said magnetic means has a gap with pole faces directed toward said gap, said container being positioned in said gap.

10. The magnetic separation apparatus of claim 9 wherein said magnetic means comprises each disposed exteriorly of said container adjacent said interior surface, the number of said pole faces being in the range of 8 to 64 faces disposed circumferentially of the axis of the passage.

11. The magnetic separation apparatus of claim 10 wherein the centers of the pole faces are spaced apart by a distance not less than the distance between the faces and said interior surface.

12. The magnetic separation apparatus of claim 5 in combination with a container, wherein said container has thin wall section providing said interior surface, said thin wall section having a wall thickness in the range of 0.635mm to 0.100 mm.

13. The magnetic separation apparatus of claim 12 wherein said wall thickness is approximately 0.100 mm.

\* \* \* \* \*